(12) United States Patent
Gyrn et al.

(10) Patent No.: US 11,786,653 B2
(45) Date of Patent: Oct. 17, 2023

(54) INSERTION DEVICE

(71) Applicant: UnoMedical A/S, Lejre (DK)

(72) Inventors: Steffen Gyrn, Ringsted (DK); Søren Thorup, Frederiksberg (DK)

(73) Assignee: Unomedical A/S, Lejre (DK)

( * ) Notice: Subject to any disclaimer, the term of this patent is extended or adjusted under 35 U.S.C. 154(b) by 0 days.

(21) Appl. No.: 15/205,949

(22) Filed: Jul. 8, 2016

(65) Prior Publication Data

US 2017/0035964 A1    Feb. 9, 2017

Related U.S. Application Data

(63) Continuation of application No. 13/583,310, filed as application No. PCT/EP2011/054910 on Mar. 30, 2011, now Pat. No. 9,415,159.

(Continued)

(30) Foreign Application Priority Data

Mar. 30, 2010   (EP) .................................... 10158465

(51) Int. Cl.
*A61M 5/158*    (2006.01)
*A61M 25/02*    (2006.01)

(52) U.S. Cl.
CPC ..... *A61M 5/158* (2013.01); *A61M 2005/1581* (2013.01); *A61M 2005/1585* (2013.01);
(Continued)

(58) Field of Classification Search
CPC .......... A61M 5/158; A61M 2005/1585; A61M 2025/028; A61M 2005/1581;
(Continued)

(56) References Cited

U.S. PATENT DOCUMENTS

| 1,592,462 A | 7/1926 | MacGregor |
| 2,047,010 A | 7/1936 | Dickinson |

(Continued)

FOREIGN PATENT DOCUMENTS

| DE | 4342329 A1 | 6/1994 |
| DE | 19631921 A1 | 3/1997 |

(Continued)

OTHER PUBLICATIONS

PCT Patent Application No. PCT/EP2011/054910 International Preliminary Report on Patentability completed Jun. 8, 2012.
(Continued)

*Primary Examiner* — Kevin C Sirmons
*Assistant Examiner* — William R Frehe
(74) *Attorney, Agent, or Firm* — Taft Stettinius & Hollister LLP; Ryan O. White; Derek B. Lavender

(57) ABSTRACT

The invention concerns a medical device provided with an outer part or shell and an inner functional part which inner functional part comprises a combination of units. The functional combination of units normally constitutes a device comprising a part being able to penetrate the skin of a patient i.e. a subcutaneous part such as a cannula, a sensor, an insertion needle or the like. Examples of such medical devices are inserter devices and infusion devices where each device comprises an outer part and an inner functional part according to claim 1. The invention relates to a medical device comprising an outer part and an inner part which outer part provides a functional cover and which inner part comprises one or more units being protected by the functional cover during use, the outer part comprises one or more activation points (56, 115) on the outer surface and the activation points are connected to contact surfaces of the inner part in such a way that pressure on the activation points initiates a function of the inner part. The activation point (56,
(Continued)

115) is positioned on a section (1b, 113b) of an outer shell of the outer part constituted by a hard material and a second section (1b, 113b) of the outer shell of the outer part is constituted by a hard material and between these two portions of hard material, the outer shell comprises a third section (1a, 113a) constituted by a soft and flexible material.

17 Claims, 22 Drawing Sheets

Related U.S. Application Data

(60) Provisional application No. 61/318,922, filed on Mar. 30, 2010.

(52) U.S. Cl.
CPC ............... *A61M 2005/1587* (2013.01); *A61M 2025/028* (2013.01); *A61M 2025/0246* (2013.01); *A61M 2025/0266* (2013.01)

(58) Field of Classification Search
CPC .. A61M 2005/1587; A61M 2025/0246; A61M 2025/0266; A61M 25/02; A61M 39/02; A61M 2005/14252; A61M 5/14244; A61M 2025/0248; A61M 2005/1426; A61M 2005/14268; A61M 2005/341; A61M 5/36
See application file for complete search history.

(56) References Cited

U.S. PATENT DOCUMENTS

| | | | |
|---|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Nicholas |
| 3,509,879 A | 5/1970 | Louis et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht et al. |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olson |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van Den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig, Jr. et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |

(56) References Cited

U.S. PATENT DOCUMENTS

| | | |
|---|---|---|
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teissen-Simony |
| 5,527,287 A | 6/1996 | Miskinyar |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili et al. |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall et al. |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple, Jr. |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rhinehart et al. |
| 5,951,523 A | 9/1999 | Oesterlind et al. |
| 5,954,643 A | 9/1999 | Vanantwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Petersen et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stradella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. et al. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse, Jr. et al. |
| 6,378,218 B2 | 4/2002 | Sigwart et al. |
| 6,379,335 B1 | 4/2002 | Rigon et al. |

(56) References Cited

U.S. PATENT DOCUMENTS

| | | |
|---|---|---|
| 6,387,076 B1 | 5/2002 | Landuyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Roenborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher et al. |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkinson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkinson et al. |
| 7,115,112 B2 | 10/2006 | Mogensen et al. |
| 7,137,968 B1 | 11/2006 | Burrell et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow et al. |
| 7,322,473 B2 | 1/2008 | Fux |
| 7,407,491 B2 | 8/2008 | Fangrow et al. |
| 7,407,493 B2 | 8/2008 | Cane et al. |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III et al. |
| 8,303,549 B2 | 11/2012 | Mejlhede et al. |
| 8,323,250 B2 | 12/2012 | Chong et al. |
| 10,071,210 B2 | 9/2018 | Gray |
| 10,292,641 B2 | 5/2019 | Bureau et al. |
| 10,293,101 B2 | 5/2019 | Brewer et al. |
| 10,369,274 B2 | 8/2019 | O'Connor et al. |
| 10,369,289 B2 | 8/2019 | Cabiri et al. |
| 10,376,638 B2 | 8/2019 | Levesque et al. |
| 10,413,661 B2 | 9/2019 | Kamen et al. |
| 10,432,403 B2 | 10/2019 | Moskal |
| 10,434,245 B2 | 10/2019 | Yodfat et al. |
| 10,434,247 B2 | 10/2019 | Cole et al. |
| 10,434,253 B2 | 10/2019 | DiPerna et al. |
| 10,434,285 B2 | 10/2019 | Schoonmaker et al. |
| 10,438,696 B2 | 10/2019 | Shapley et al. |
| 10,441,356 B2 | 10/2019 | Zarins et al. |
| 10,441,718 B2 | 10/2019 | Tchao et al. |
| 10,441,775 B2 | 10/2019 | Schriver et al. |
| 10,449,290 B2 | 10/2019 | Shapley et al. |
| 10,449,306 B2 | 10/2019 | Grover et al. |
| 10,463,785 B2 | 11/2019 | Dewey |
| 10,463,791 B2 | 11/2019 | Shergold et al. |
| 10,471,203 B2 | 11/2019 | Chappel et al. |
| 10,471,206 B2 | 11/2019 | Dittrich |
| 10,478,550 B2 | 11/2019 | Hadvary et al. |
| 10,478,552 B2 | 11/2019 | Cronenberg et al. |
| 10,478,554 B2 | 11/2019 | Bazargan et al. |
| 10,478,555 B2 | 11/2019 | Radojicic |
| 10,483,000 B2 | 11/2019 | Saint et al. |
| 10,485,923 B2 | 11/2019 | Schiendzielorz |
| 10,485,937 B2 | 11/2019 | Yodfat et al. |
| 10,489,617 B2 | 11/2019 | Salem et al. |
| 10,493,201 B2 | 12/2019 | Cole et al. |
| 10,493,202 B2 | 12/2019 | Hayter |
| 10,493,203 B2 | 12/2019 | Yodfat et al. |
| 10,500,352 B2 | 12/2019 | Grant et al. |
| 10,507,316 B2 | 12/2019 | Fielder et al. |
| 10,512,724 B2 | 12/2019 | Renstad et al. |
| 10,525,193 B2 | 1/2020 | Schauderna |
| 10,525,247 B2 | 1/2020 | Bellrichard et al. |
| 10,532,150 B2 | 1/2020 | Bazargan et al. |
| 10,532,151 B2 | 1/2020 | Wei |
| 10,532,155 B2 | 1/2020 | Schiendzielorz |
| 10,532,159 B2 | 1/2020 | Tornsten et al. |
| 10,532,835 B2 | 1/2020 | Chong et al. |
| 10,537,681 B2 | 1/2020 | Tan-Malecki et al. |
| 10,539,481 B2 | 1/2020 | Plahey et al. |
| 10,542,936 B2 | 1/2020 | Goldberg et al. |
| 10,549,029 B2 | 2/2020 | Agard et al. |
| 10,549,033 B2 | 2/2020 | Shimizu |
| 10,549,034 B2 | 2/2020 | Eggert et al. |
| 10,549,036 B2 | 2/2020 | Starkweather et al. |

(56) References Cited

U.S. PATENT DOCUMENTS

| | | |
|---|---|---|
| 10,549,079 B2 | 2/2020 | Burton et al. |
| 10,556,059 B2 | 2/2020 | Cross et al. |
| 10,556,063 B2 | 2/2020 | Murphy, Jr. et al. |
| 10,561,785 B2 | 2/2020 | Roy et al. |
| 10,561,789 B2 | 2/2020 | Mastrototaro et al. |
| 10,561,826 B2 | 2/2020 | Amano et al. |
| 10,561,831 B2 | 2/2020 | Kato |
| 10,569,011 B2 | 2/2020 | Dilanni et al. |
| 10,569,012 B2 | 2/2020 | Schabbach et al. |
| 10,569,014 B2 | 2/2020 | Hanson et al. |
| 10,576,203 B2 | 3/2020 | Amon et al. |
| 10,576,204 B2 | 3/2020 | Estes et al. |
| 10,583,241 B2 | 3/2020 | Wu et al. |
| 10,583,247 B2 | 3/2020 | Mandro |
| 10,589,023 B2 | 3/2020 | Cindrich et al. |
| 10,589,028 B2 | 3/2020 | Cabiri et al. |
| 10,596,317 B2 | 3/2020 | Nakanishi |
| 10,596,362 B2 | 3/2020 | Fielder et al. |
| 10,610,638 B2 | 4/2020 | Cabiri et al. |
| 10,617,817 B2 | 4/2020 | Hwang et al. |
| 10,617,820 B2 | 4/2020 | O'Connor et al. |
| 10,625,016 B2 | 4/2020 | Amon et al. |
| 10,625,017 B2 | 4/2020 | Searle et al. |
| 10,625,018 B2 | 4/2020 | Destefano et al. |
| 10,632,248 B2 | 4/2020 | Stefanov et al. |
| 10,632,249 B2 | 4/2020 | Marbet et al. |
| 10,632,253 B2 | 4/2020 | Uchiyama et al. |
| 10,632,256 B2 | 4/2020 | Sasaki |
| 10,632,257 B2 | 4/2020 | Estes et al. |
| 10,635,784 B2 | 4/2020 | Rubalcaba, Jr. et al. |
| 10,639,418 B2 | 5/2020 | Kamen et al. |
| 10,639,661 B2 | 5/2020 | Fontana |
| 10,646,643 B2 | 5/2020 | Cabiri et al. |
| 10,646,652 B2 | 5/2020 | McCullough et al. |
| 10,646,653 B2 | 5/2020 | Despa et al. |
| 10,653,828 B2 | 5/2020 | Brown et al. |
| 10,653,833 B2 | 5/2020 | Kamen et al. |
| 10,653,835 B2 | 5/2020 | Dobbles et al. |
| 10,653,846 B2 | 5/2020 | Weibel et al. |
| 10,661,006 B2 | 5/2020 | Antonio et al. |
| 10,661,007 B2 | 5/2020 | Estes |
| 10,661,008 B2 | 5/2020 | Brewer et al. |
| 10,661,067 B2 | 5/2020 | Kodama |
| 10,668,210 B2 | 6/2020 | Kamen et al. |
| 10,668,213 B2 | 6/2020 | Cabiri |
| 10,668,227 B2 | 6/2020 | Caspers |
| 10,675,055 B2 | 6/2020 | Chong et al. |
| 10,675,333 B2 | 6/2020 | Ning et al. |
| 10,675,404 B2 | 6/2020 | Pizzochero et al. |
| 10,682,458 B2 | 6/2020 | Wu et al. |
| 10,682,460 B2 | 6/2020 | Adams et al. |
| 10,682,461 B2 | 6/2020 | Oakes |
| 10,682,463 B2 | 6/2020 | Kamen et al. |
| 10,685,749 B2 | 6/2020 | Hayter et al. |
| 10,688,241 B2 | 6/2020 | Yang |
| 10,688,243 B2 | 6/2020 | Cabiri |
| 10,688,294 B2 | 6/2020 | Cowan et al. |
| 10,716,891 B2 | 7/2020 | Saab et al. |
| 10,716,893 B2 | 7/2020 | Gray et al. |
| 10,716,895 B2 | 7/2020 | Brewer et al. |
| 10,716,896 B2 | 7/2020 | O'Connor et al. |
| 10,716,926 B2 | 7/2020 | Burton et al. |
| 10,719,584 B2 | 7/2020 | Drew |
| 10,722,643 B2 | 7/2020 | Gray et al. |
| 10,722,646 B2 | 7/2020 | Cole et al. |
| 10,722,647 B2 | 7/2020 | Gray |
| 10,722,650 B2 | 7/2020 | Duke et al. |
| 10,722,661 B2 | 7/2020 | Mandro et al. |
| 10,729,842 B2 | 8/2020 | Hooven et al. |
| 10,729,844 B2 | 8/2020 | Cole et al. |
| 10,737,015 B2 | 8/2020 | Estes |
| 10,737,016 B2 | 8/2020 | Smith et al. |
| 10,737,021 B2 | 8/2020 | Deck |
| 10,737,024 B2 | 8/2020 | Schmid |
| 10,737,026 B2 | 8/2020 | Teutsch |
| 10,737,038 B2 | 8/2020 | Cole et al. |
| 10,744,257 B2 | 8/2020 | Mandro et al. |
| 10,751,467 B2 | 8/2020 | Kamen et al. |
| 10,751,468 B2 | 8/2020 | Abal |
| 10,751,476 B2 | 8/2020 | Gazeley et al. |
| 10,757,219 B2 | 8/2020 | Moskal |
| 10,758,683 B2 | 9/2020 | Gibson et al. |
| 10,758,721 B2 | 9/2020 | Sonderegger et al. |
| 10,765,801 B2 | 9/2020 | McCullough |
| 10,765,803 B2 | 9/2020 | Gonnelli |
| 10,772,796 B2 | 9/2020 | Kavazov |
| 10,773,019 B2 | 9/2020 | Searle et al. |
| 10,780,215 B2 | 9/2020 | Rosinko et al. |
| 10,780,216 B2 | 9/2020 | Farra |
| 10,780,220 B2 | 9/2020 | Gray |
| 10,780,223 B2 | 9/2020 | Desborough et al. |
| 10,792,419 B2 | 10/2020 | Kamen et al. |
| 10,792,424 B2 | 10/2020 | Sasaki |
| 10,792,440 B2 | 10/2020 | Mandro et al. |
| 10,799,630 B2 | 10/2020 | McCullough |
| 10,799,631 B2 | 10/2020 | Barmaimon et al. |
| 10,799,632 B2 | 10/2020 | Kohlbrecher |
| 10,806,851 B2 | 10/2020 | Rosinko |
| 10,806,854 B2 | 10/2020 | O'Connor et al. |
| 10,806,855 B2 | 10/2020 | Destefano et al. |
| 10,806,859 B2 | 10/2020 | Desborough et al. |
| 10,814,061 B2 | 10/2020 | Bene et al. |
| 11,027,058 B2 | 6/2021 | Lanier, Jr. et al. |
| 11,052,189 B2 | 7/2021 | Searle et al. |
| 11,135,362 B2 | 10/2021 | DiPerna et al. |
| 11,136,971 B2 | 10/2021 | Kamen et al. |
| 11,136,972 B2 | 10/2021 | Kamen et al. |
| 11,241,534 B2 | 2/2022 | Miller et al. |
| 11,261,858 B2 | 3/2022 | Kamen et al. |
| 11,293,425 B2 | 4/2022 | Kamen et al. |
| 11,318,249 B2 | 5/2022 | Kamen et al. |
| 11,339,774 B2 | 5/2022 | Gray et al. |
| 11,357,910 B2 | 6/2022 | Kamen et al. |
| 11,364,335 B2 | 6/2022 | Lanigan et al. |
| 11,391,273 B2 | 7/2022 | Kamen et al. |
| 11,404,776 B2 | 8/2022 | Blumberg, Jr. |
| 11,406,753 B2 | 8/2022 | Gray et al. |
| 11,408,414 B2 | 8/2022 | Kamen et al. |
| 11,413,391 B2 | 8/2022 | Gray |
| 11,471,592 B2 | 10/2022 | Searle, II et al. |
| 11,478,623 B2 | 10/2022 | Lanigan et al. |
| 11,491,273 B2 | 11/2022 | Gray |
| 11,497,846 B2 | 11/2022 | Kamen et al. |
| 11,497,850 B2 | 11/2022 | Hanson et al. |
| 11,534,543 B2 | 12/2022 | Kamen et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer et al. |
| 2001/0053889 A1 | 12/2001 | Marggi et al. |
| 2001/0056284 A1 | 12/2001 | Purcell et al. |
| 2002/0022798 A1 | 2/2002 | Connelly et al. |
| 2002/0022855 A1 | 2/2002 | Bobroff et al. |
| 2002/0026152 A1 | 2/2002 | Bierman |
| 2002/0055711 A1* | 5/2002 | Lavi .................... A61M 5/326 |
| | | 604/110 |
| 2002/0068904 A1 | 6/2002 | Bierman et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0095138 A1 | 7/2002 | Lynch et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |

(56) References Cited

U.S. PATENT DOCUMENTS

| | | |
|---|---|---|
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel et al. |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0055711 A1 | 3/2004 | Martin et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia et al. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane et al. |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow et al. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson et al. |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Buetikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen et al. |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld et al. |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld et al. |
| 2006/0142698 A1 | 6/2006 | Ethelfeld et al. |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney et al. |
| 2006/0184140 A1 | 8/2006 | Okiyama |
| 2006/0200073 A1 | 9/2006 | Radmer et al. |
| 2006/0211990 A1 | 9/2006 | Fangrow et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0088271 A1 | 4/2007 | Richards |
| 2007/0093754 A1 | 4/2007 | Mogensen et al. |
| 2007/0104596 A1 | 5/2007 | Preuthun et al. |
| 2007/0112301 A1 | 5/2007 | Preuthun et al. |
| 2007/0112303 A1 | 5/2007 | Liniger et al. |
| 2007/0124002 A1 | 5/2007 | Estes et al. |
| 2007/0129688 A1 | 6/2007 | Scheurer et al. |
| 2007/0129691 A1 | 6/2007 | Sage et al. |
| 2007/0173767 A1 | 7/2007 | Lynch et al. |
| 2007/0179444 A1 | 8/2007 | Causey et al. |
| 2007/0185441 A1 | 8/2007 | Fangrow et al. |
| 2007/0191770 A1 | 8/2007 | Moberg et al. |
| 2007/0191772 A1 | 8/2007 | Wojcik |
| 2007/0191773 A1 | 8/2007 | Wojcik |

(56) References Cited

U.S. PATENT DOCUMENTS

| | | |
|---|---|---|
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0282269 A1 | 12/2007 | Carter et al. |
| 2007/0299409 A1 | 12/2007 | Whitbourne et al. |
| 2008/0051692 A1 | 2/2008 | Petersen et al. |
| 2008/0058692 A1 | 3/2008 | Propp et al. |
| 2008/0200897 A1 | 8/2008 | Hoss et al. |
| 2008/0215035 A1 | 9/2008 | Yodfat et al. |
| 2008/0234630 A1 | 9/2008 | Iddan et al. |
| 2008/0269687 A1* | 10/2008 | Chong ............... A61M 5/1413 604/180 |
| 2008/0312601 A1 | 12/2008 | Cane |
| 2009/0062767 A1 | 3/2009 | Van Antwerp et al. |
| 2009/0124979 A1* | 5/2009 | Raymond ......... A61M 5/14244 604/195 |
| 2009/0326453 A1 | 12/2009 | Adams et al. |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0049128 A1 | 2/2010 | McKenzie et al. |
| 2010/0094251 A1 | 4/2010 | Estes |
| 2010/0135831 A1 | 6/2010 | Jacobsen |
| 2010/0137829 A1 | 6/2010 | Nielsen et al. |
| 2010/0145303 A1 | 6/2010 | Yodfat et al. |
| 2010/0168670 A1 | 7/2010 | Srisathapat et al. |
| 2010/0228226 A1 | 9/2010 | Nielsen |
| 2010/0241103 A1 | 9/2010 | Kraft et al. |
| 2010/0262078 A1 | 10/2010 | Blomquist |
| 2011/0040247 A1 | 2/2011 | Mandro et al. |
| 2011/0054399 A1 | 3/2011 | Chong et al. |
| 2011/0060287 A1 | 3/2011 | Ambruzs et al. |
| 2011/0112484 A1 | 5/2011 | Carter et al. |
| 2011/0112696 A1 | 5/2011 | Yodfat et al. |
| 2011/0118578 A1 | 5/2011 | Timmerman |
| 2011/0160652 A1 | 6/2011 | Yodfat et al. |
| 2011/0160666 A1 | 6/2011 | Hanson et al. |
| 2011/0313357 A1 | 12/2011 | Skutnik et al. |
| 2012/0078170 A1 | 3/2012 | Smith et al. |
| 2012/0095406 A1* | 4/2012 | Gyrn ..................... A61M 5/158 604/164.08 |
| 2012/0136300 A1 | 5/2012 | Schoonmaker et al. |
| 2012/0150123 A1 | 6/2012 | Lawrence et al. |
| 2012/0209085 A1 | 8/2012 | Degen et al. |
| 2012/0238851 A1 | 9/2012 | Kamen et al. |
| 2013/0046239 A1 | 2/2013 | Gonnelli et al. |
| 2013/0046508 A1 | 2/2013 | Sur et al. |
| 2013/0053823 A1 | 2/2013 | Fiering et al. |
| 2013/0060233 A1 | 3/2013 | O'Connor et al. |
| 2013/0079719 A1* | 3/2013 | Gyrn ..................... A61M 5/158 604/134 |
| 2013/0138075 A1 | 5/2013 | Lambert |
| 2013/0226138 A1 | 8/2013 | Sia |
| 2013/0237918 A1* | 9/2013 | Gyrn ................ A61B 17/3468 604/164.12 |
| 2013/0237955 A1 | 9/2013 | Neta et al. |
| 2014/0025002 A1 | 1/2014 | Qi et al. |
| 2014/0031793 A1 | 1/2014 | Constantineau et al. |
| 2014/0052096 A1 | 2/2014 | Searle et al. |
| 2014/0054883 A1 | 2/2014 | Lanigan et al. |
| 2014/0127048 A1 | 5/2014 | Dilanni et al. |
| 2014/0128815 A1 | 5/2014 | Cabiri et al. |
| 2014/0276379 A1 | 9/2014 | Uram et al. |
| 2014/0276536 A1 | 9/2014 | Estes |
| 2014/0323961 A1 | 10/2014 | Blomquist et al. |
| 2014/0358112 A1 | 12/2014 | Smith et al. |
| 2015/0025503 A1 | 1/2015 | Searle et al. |
| 2015/0073384 A1 | 3/2015 | Limaye |
| 2015/0080799 A1 | 3/2015 | Schneider et al. |
| 2015/0080800 A1 | 3/2015 | Cronenberg |
| 2015/0105720 A1 | 4/2015 | Montalvo et al. |
| 2015/0112269 A1 | 4/2015 | Sumida et al. |
| 2015/0209505 A1 | 7/2015 | Hanson et al. |
| 2015/0273201 A1 | 10/2015 | Tallarida et al. |
| 2015/0314117 A1 | 11/2015 | Arami et al. |
| 2016/0051750 A1 | 2/2016 | Tsoukalis |
| 2016/0074578 A1 | 3/2016 | Xu et al. |
| 2016/0082182 A1 | 3/2016 | Gregory et al. |
| 2016/0089056 A1 | 3/2016 | Limaye et al. |
| 2016/0089524 A1 | 3/2016 | Anderson |
| 2016/0144105 A1 | 5/2016 | Hooven et al. |
| 2016/0193407 A1 | 7/2016 | Qin et al. |
| 2016/0346469 A1 | 12/2016 | Shubinsky et al. |
| 2017/0080157 A1 | 3/2017 | Cabiri et al. |
| 2017/0100542 A1 | 4/2017 | Norton et al. |
| 2017/0232191 A1 | 8/2017 | Smith et al. |
| 2017/0258987 A1 | 9/2017 | Caspers |
| 2017/0290971 A1 | 10/2017 | Hedmann et al. |
| 2017/0296741 A1 | 10/2017 | Gregory |
| 2017/0296742 A1 | 10/2017 | Stefanov |
| 2017/0340827 A1 | 11/2017 | Nazzaro et al. |
| 2017/0340841 A1 | 11/2017 | Sasaki |
| 2017/0351841 A1 | 12/2017 | Moskal |
| 2017/0351851 A1 | 12/2017 | Wang et al. |
| 2017/0368260 A1 | 12/2017 | McCullough et al. |
| 2018/0028744 A1 | 2/2018 | Kim |
| 2018/0036476 A1 | 2/2018 | McCullough et al. |
| 2018/0071450 A1 | 3/2018 | Ruhland |
| 2018/0110420 A1 | 4/2018 | Pekander |
| 2018/0185573 A1 | 7/2018 | Niklaus |
| 2018/0221571 A1 | 8/2018 | Carbone et al. |
| 2018/0344926 A1 | 12/2018 | Brandenburg et al. |
| 2018/0361061 A1 | 12/2018 | Andretta |
| 2018/0372085 A1 | 12/2018 | Velschow et al. |
| 2019/0009022 A1 | 1/2019 | Oakes |
| 2019/0083057 A1 | 3/2019 | Saul et al. |
| 2019/0262535 A1 | 8/2019 | Shubinsky et al. |
| 2019/0298485 A1 | 10/2019 | Forsell |
| 2019/0298912 A1 | 10/2019 | Spencer et al. |
| 2019/0298914 A1 | 10/2019 | Kamen et al. |
| 2019/0298921 A1 | 10/2019 | Stafford |
| 2019/0307943 A1 | 10/2019 | Franano et al. |
| 2019/0307955 A1 | 10/2019 | Levesque et al. |
| 2019/0307970 A1 | 10/2019 | Kamen et al. |
| 2019/0321545 A1 | 10/2019 | Saint |
| 2019/0321552 A1 | 10/2019 | DiPerna et al. |
| 2019/0336678 A1 | 11/2019 | Rule |
| 2019/0336681 A1 | 11/2019 | Kamen et al. |
| 2019/0343434 A1 | 11/2019 | Varsavsky et al. |
| 2019/0344010 A1 | 11/2019 | Pizzochero et al. |
| 2019/0350501 A1 | 11/2019 | Blomquist et al. |
| 2019/0351134 A1 | 11/2019 | Cook et al. |
| 2019/0351209 A1 | 11/2019 | Butziger et al. |
| 2019/0358395 A1 | 11/2019 | Olson et al. |
| 2019/0358437 A1 | 11/2019 | Schwartz et al. |
| 2019/0366012 A1 | 12/2019 | Gross et al. |
| 2019/0368484 A1 | 12/2019 | Chappel et al. |
| 2019/0374709 A1 | 12/2019 | Cole et al. |
| 2019/0374714 A1 | 12/2019 | Rioux et al. |
| 2019/0374719 A1 | 12/2019 | Cabiri et al. |
| 2019/0374757 A1 | 12/2019 | Verhoeven et al. |
| 2019/0381241 A1 | 12/2019 | Bryant et al. |
| 2019/0388609 A1 | 12/2019 | Lanigan et al. |
| 2019/0388614 A1 | 12/2019 | Gyrn et al. |
| 2019/0388615 A1* | 12/2019 | Sonderegger ....... A61M 25/065 |
| 2020/0001005 A1 | 1/2020 | Politis et al. |
| 2020/0001006 A1 | 1/2020 | Pizzochero et al. |
| 2020/0001007 A1 | 1/2020 | Miesel et al. |
| 2020/0009317 A1 | 1/2020 | Cronenberg et al. |
| 2020/0009318 A1 | 1/2020 | Kamen et al. |
| 2020/0009319 A1 | 1/2020 | Ludolph |
| 2020/0009331 A1 | 1/2020 | Kamen et al. |
| 2020/0016335 A1 | 1/2020 | DiPerna et al. |
| 2020/0023121 A1 | 1/2020 | Thomas et al. |
| 2020/0023129 A1 | 1/2020 | Day et al. |
| 2020/0030528 A1 | 1/2020 | Burke et al. |
| 2020/0030531 A1 | 1/2020 | Day et al. |
| 2020/0030532 A1 | 1/2020 | Day et al. |
| 2020/0030533 A1 | 1/2020 | Day et al. |
| 2020/0030592 A1 | 1/2020 | Cheche |
| 2020/0038588 A1 | 2/2020 | Varsavsky et al. |
| 2020/0054822 A1 | 2/2020 | Dewey |
| 2020/0054825 A1 | 2/2020 | Kamen et al. |

(56) References Cited

U.S. PATENT DOCUMENTS

| | | |
|---|---|---|
| 2020/0054826 A1 | 2/2020 | Diianni et al. |
| 2020/0061287 A1 | 2/2020 | Chappel et al. |
| 2020/0069865 A1 | 3/2020 | Day et al. |
| 2020/0069869 A1 | 3/2020 | Grant et al. |
| 2020/0077340 A1 | 3/2020 | Kruse |
| 2020/0077948 A1 | 3/2020 | Schmid |
| 2020/0078511 A1 | 3/2020 | Focht et al. |
| 2020/0078513 A1 | 3/2020 | Wei |
| 2020/0086042 A1 | 3/2020 | Kamen et al. |
| 2020/0086043 A1 | 3/2020 | Saint |
| 2020/0101218 A1 | 4/2020 | Shapley et al. |
| 2020/0101226 A1 | 4/2020 | Rosinko et al. |
| 2020/0114069 A1 | 4/2020 | Searle et al. |
| 2020/0118676 A1 | 4/2020 | Spohn et al. |
| 2020/0121854 A1 | 4/2020 | Norton et al. |
| 2020/0121937 A1 | 4/2020 | Yoder et al. |
| 2020/0138852 A1 | 5/2020 | Chattaraj et al. |
| 2020/0138911 A1 | 5/2020 | Joseph et al. |
| 2020/0147304 A1 | 5/2020 | Crouther et al. |
| 2020/0147305 A1 | 5/2020 | Estes |
| 2020/0147309 A1 | 5/2020 | Quinn et al. |
| 2020/0164159 A1 | 5/2020 | Chattaraj et al. |
| 2020/0168316 A1 | 5/2020 | Kamen |
| 2020/0171236 A1 | 6/2020 | McCullough et al. |
| 2020/0179592 A1 | 6/2020 | Adams et al. |
| 2020/0179594 A1 | 6/2020 | Yodfat et al. |
| 2020/0179602 A1 | 6/2020 | Mazlish |
| 2020/0179603 A1 | 6/2020 | Rosinko |
| 2020/0188580 A1 | 6/2020 | Gregory et al. |
| 2020/0188581 A1 | 6/2020 | Diianni et al. |
| 2020/0188588 A1 | 6/2020 | Estes |
| 2020/0197600 A1 | 6/2020 | Chow et al. |
| 2020/0197621 A1 | 6/2020 | Quinn et al. |
| 2020/0206418 A1 | 7/2020 | Gonnelli et al. |
| 2020/0215264 A1 | 7/2020 | Searle et al. |
| 2020/0215273 A1 | 7/2020 | Gibson et al. |
| 2020/0222624 A1 | 7/2020 | Destefano et al. |
| 2020/0222625 A1 | 7/2020 | Cabiri et al. |
| 2020/0230314 A1 | 7/2020 | Kondo et al. |
| 2020/0246541 A1 | 8/2020 | Neftel et al. |
| 2020/0253632 A1 | 8/2020 | Chong et al. |
| 2020/0254174 A1 | 8/2020 | Kruse et al. |
| 2020/0261002 A1 | 8/2020 | Pace |
| 2020/0261645 A1 | 8/2020 | Kamen et al. |
| 2020/0268962 A1 | 8/2020 | Gamelin |
| 2020/0268975 A1 | 8/2020 | Kim et al. |
| 2020/0272310 A1 | 8/2020 | Vik et al. |
| 2020/0276386 A1 | 9/2020 | Kamen et al. |
| 2020/0306446 A1 | 10/2020 | Kamen et al. |
| 2020/0306448 A1 | 10/2020 | Schmid |
| 2020/0316291 A1 | 10/2020 | Gibson et al. |
| 2020/0321094 A1 | 10/2020 | Saint et al. |
| 2020/0324048 A1 | 10/2020 | O'Connor et al. |
| 2020/0324101 A1 | 10/2020 | Hartmann et al. |
| 2020/0330679 A1 | 10/2020 | Cronenberg et al. |
| 2020/0330680 A1 | 10/2020 | Deck |
| 2020/0330701 A1 | 10/2020 | Cole et al. |
| 2020/0335194 A1 | 10/2020 | Jacobson et al. |
| 2020/0338257 A1 | 10/2020 | Hooven et al. |
| 2020/0338262 A1 | 10/2020 | Kamen et al. |
| 2020/0338266 A1 | 10/2020 | Estes |
| 2021/0060241 A1 | 3/2021 | Kamen et al. |
| 2021/0170097 A1 | 6/2021 | Kamen et al. |
| 2021/0180583 A1 | 6/2021 | Gray |
| 2021/0180584 A1 | 6/2021 | Kamen et al. |
| 2021/0190063 A1 | 6/2021 | Gray |
| 2021/0228798 A1 | 7/2021 | Kamen et al. |
| 2021/0236721 A1 | 8/2021 | Skutnik et al. |
| 2021/0268174 A1 | 9/2021 | Estes et al. |
| 2021/0270255 A1 | 9/2021 | Gray |
| 2021/0293232 A1 | 9/2021 | Kamen et al. |
| 2021/0308367 A1 | 10/2021 | Searle et al. |
| 2021/0321914 A1 | 10/2021 | Brister et al. |
| 2021/0338926 A1 | 11/2021 | Kamen et al. |
| 2021/0361858 A1 | 11/2021 | Lanier, Jr. et al. |
| 2021/0393870 A1 | 12/2021 | Kessel et al. |
| 2021/0396221 A1 | 12/2021 | Kamen et al. |
| 2022/0001106 A1 | 1/2022 | DiPerna et al. |
| 2022/0184303 A1 | 6/2022 | DiPerna et al. |
| 2022/0211937 A1 | 7/2022 | Kamen et al. |
| 2022/0249769 A1 | 8/2022 | Kamen et al. |
| 2022/0265918 A1 | 8/2022 | Kamen et al. |
| 2022/0275796 A9 | 9/2022 | Kamen et al. |
| 2022/0280715 A1 | 9/2022 | Gray et al. |
| 2022/0379013 A1 | 12/2022 | Kamen et al. |

FOREIGN PATENT DOCUMENTS

| | | |
|---|---|---|
| DE | 29905072 U1 | 9/1999 |
| DE | 10117285 A1 | 11/2002 |
| DE | 20320207 U1 | 10/2004 |
| EP | 0272530 A2 | 6/1988 |
| EP | 0117632 B1 | 8/1989 |
| EP | 0239244 B1 | 9/1991 |
| EP | 0451040 A1 | 10/1991 |
| EP | 0615768 A2 | 9/1994 |
| EP | 0652027 A1 | 5/1995 |
| EP | 0657184 A1 | 6/1995 |
| EP | 0744183 A2 | 11/1996 |
| EP | 0747006 A1 | 12/1996 |
| EP | 0799626 A1 | 10/1997 |
| EP | 0544837 B1 | 11/1997 |
| EP | 0688232 B1 | 12/1998 |
| EP | 0937475 A2 | 8/1999 |
| EP | 0651662 B1 | 9/1999 |
| EP | 0956879 A1 | 11/1999 |
| EP | 1086718 A1 | 3/2001 |
| EP | 1125593 A1 | 8/2001 |
| EP | 0775501 B1 | 6/2002 |
| EP | 0714631 B1 | 12/2002 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1329233 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| EP | 2272559 A1 | 1/2011 |
| EP | 3705149 B1 | 9/2021 |
| EP | 3881874 A1 | 9/2021 |
| EP | 3406278 B1 | 10/2021 |
| EP | 3912657 A1 | 11/2021 |
| EP | 2995330 B1 | 12/2021 |
| EP | 2155299 B1 | 1/2022 |
| EP | 3988147 A1 | 4/2022 |
| EP | 2611478 B1 | 8/2022 |
| EP | 3470100 B1 | 8/2022 |
| FR | 2725902 A1 | 4/1996 |
| FR | 2752164 A1 | 2/1998 |
| GB | 906574 A | 9/1962 |
| GB | 2088215 A | 6/1982 |
| GB | 2230702 A | 10/1990 |
| GB | 2423267 A | 8/2006 |
| GB | 2450872 A | 1/2009 |
| GB | 2459101 A | 10/2009 |
| JP | H03191965 A | 8/1991 |
| JP | H0751251 A | 2/1995 |
| JP | H08187286 A | 7/1996 |
| JP | H10179734 A | 7/1998 |
| JP | 2002028246 A | 1/2002 |

(56) References Cited

FOREIGN PATENT DOCUMENTS

| | | |
|---|---|---|
| RU | 2238111 C2 | 10/2004 |
| SU | 933100 A1 | 6/1982 |
| WO | WO-8101795 A1 | 7/1981 |
| WO | WO-8203558 A1 | 10/1982 |
| WO | WO-9204062 A1 | 3/1992 |
| WO | WO-9305840 A2 | 4/1993 |
| WO | WO-9311709 A1 | 6/1993 |
| WO | WO-9420160 A1 | 9/1994 |
| WO | WO-9519194 A1 | 7/1995 |
| WO | WO-9620021 A1 | 7/1996 |
| WO | WO-9632981 A1 | 10/1996 |
| WO | WO-9826835 A1 | 6/1998 |
| WO | WO-9833549 A1 | 8/1998 |
| WO | WO-9858693 A1 | 12/1998 |
| WO | WO-9907435 A1 | 2/1999 |
| WO | WO-9922789 A1 | 5/1999 |
| WO | WO-9933504 A1 | 7/1999 |
| WO | WO-0002614 A1 | 1/2000 |
| WO | WO-0003757 A1 | 1/2000 |
| WO | WO-0044324 A1 | 8/2000 |
| WO | WO-0112746 A1 | 2/2001 |
| WO | WO-0130419 A2 | 5/2001 |
| WO | WO-0168180 A1 | 9/2001 |
| WO | WO-0172353 A2 | 10/2001 |
| WO | WO-0176684 A1 | 10/2001 |
| WO | WO-0193926 A2 | 12/2001 |
| WO | WO-0202165 A2 | 1/2002 |
| WO | WO-0207804 A1 | 1/2002 |
| WO | WO-0240083 A2 | 5/2002 |
| WO | WO-02053220 A2 | 7/2002 |
| WO | WO-02068014 A2 | 9/2002 |
| WO | WO-02081012 A2 | 10/2002 |
| WO | WO-02081013 A2 | 10/2002 |
| WO | WO-02083206 A2 | 10/2002 |
| WO | WO-02083228 A2 | 10/2002 |
| WO | WO-02094352 A2 | 11/2002 |
| WO | WO-02100457 A2 | 12/2002 |
| WO | WO-02102442 A1 | 12/2002 |
| WO | WO-03015860 A1 | 2/2003 |
| WO | WO-03026728 A1 | 4/2003 |
| WO | WO-03068305 A1 | 8/2003 |
| WO | WO-03075980 A2 | 9/2003 |
| WO | WO-03095003 A1 | 11/2003 |
| WO | WO-2004012796 A1 | 2/2004 |
| WO | WO-2004024219 A1 | 3/2004 |
| WO | WO-2004026375 A1 | 4/2004 |
| WO | WO-2004029457 A1 | 4/2004 |
| WO | WO-2004030726 A1 | 4/2004 |
| WO | WO-2004037325 A1 | 5/2004 |
| WO | WO-2004054644 A1 | 7/2004 |
| WO | WO-2004056412 A2 | 7/2004 |
| WO | WO-2004064593 A2 | 8/2004 |
| WO | WO-2004071308 A1 | 8/2004 |
| WO | WO-2004087240 A1 | 10/2004 |
| WO | WO-2004098683 A1 | 11/2004 |
| WO | WO-2004101016 A1 | 11/2004 |
| WO | WO-2004101071 A2 | 11/2004 |
| WO | WO-2004110527 A1 | 12/2004 |
| WO | WO-2005002649 A1 | 1/2005 |
| WO | WO-2005004973 A1 | 1/2005 |
| WO | WO-2005018703 A2 | 3/2005 |
| WO | WO-2005037184 A2 | 4/2005 |
| WO | WO-2005037350 A2 | 4/2005 |
| WO | WO-2005039673 A2 | 5/2005 |
| WO | WO-2005046780 A1 | 5/2005 |
| WO | WO-2005065748 A1 | 7/2005 |
| WO | WO-2005068006 A1 | 7/2005 |
| WO | WO-2005072795 A2 | 8/2005 |
| WO | WO-2005092410 A1 | 10/2005 |
| WO | WO-2005094920 A1 | 10/2005 |
| WO | WO-2005112800 A2 | 12/2005 |
| WO | WO-2005118055 A1 | 12/2005 |
| WO | WO-2006003130 A1 | 1/2006 |
| WO | WO-2006015507 A2 | 2/2006 |
| WO | WO-2006015600 A2 | 2/2006 |
| WO | WO-2006024650 A2 | 3/2006 |
| WO | WO-2006032689 A1 | 3/2006 |
| WO | WO-2006032692 A1 | 3/2006 |
| WO | WO-2006061027 A2 | 6/2006 |
| WO | WO-2006061354 A1 | 6/2006 |
| WO | WO-2006062680 A1 | 6/2006 |
| WO | WO-2006062912 A1 | 6/2006 |
| WO | WO-2006075016 A1 | 7/2006 |
| WO | WO-2006077262 A1 | 7/2006 |
| WO | WO-2006077263 A1 | 7/2006 |
| WO | WO-2006089958 A1 | 8/2006 |
| WO | WO-2006097111 A2 | 9/2006 |
| WO | WO-2006108775 A2 | 10/2006 |
| WO | WO-2006120253 A2 | 11/2006 |
| WO | WO-2006121921 A2 | 11/2006 |
| WO | WO-2006122048 A1 | 11/2006 |
| WO | WO-2007000162 A2 | 1/2007 |
| WO | WO-2007002523 A2 | 1/2007 |
| WO | WO-2007020090 A1 | 2/2007 |
| WO | WO-2007065944 A1 | 6/2007 |
| WO | WO-2007071255 A1 | 6/2007 |
| WO | WO-2007071258 A1 | 6/2007 |
| WO | WO-2007093051 A1 | 8/2007 |
| WO | WO-2007093182 A2 | 8/2007 |
| WO | WO-2007122207 A1 | 11/2007 |
| WO | WO-2007140631 A1 | 12/2007 |
| WO | WO-2007140783 A2 | 12/2007 |
| WO | WO-2007140785 A1 | 12/2007 |
| WO | WO-2007141210 A1 | 12/2007 |
| WO | WO-2008014791 A1 | 2/2008 |
| WO | WO-2008014792 A1 | 2/2008 |
| WO | WO-2008048631 A1 | 4/2008 |
| WO | WO-2008052545 A1 | 5/2008 |
| WO | WO-2008065646 A1 | 6/2008 |
| WO | WO-2008092782 A1 | 8/2008 |
| WO | WO-2008092958 A2 | 8/2008 |
| WO | WO-2008092959 A1 | 8/2008 |
| WO | WO-2008133702 A1 | 11/2008 |
| WO | WO-2008135098 A1 | 11/2008 |
| WO | WO-2008147600 A1 | 12/2008 |
| WO | WO-2008148714 A1 | 12/2008 |
| WO | WO-2008155145 A1 | 12/2008 |
| WO | WO-2008155377 A1 | 12/2008 |
| WO | WO-2009004026 A1 | 1/2009 |
| WO | WO-2009007287 A1 | 1/2009 |
| WO | WO-2009010396 A1 | 1/2009 |
| WO | WO-2009010399 A1 | 1/2009 |
| WO | WO-2009016635 A2 | 2/2009 |
| WO | WO-2009033032 A1 | 3/2009 |
| WO | WO-2009039013 A1 | 3/2009 |
| WO | WO-2009098291 A1 | 8/2009 |
| WO | WO-2009098306 A1 | 8/2009 |
| WO | WO-2009101130 A1 | 8/2009 |
| WO | WO-2009101145 A1 | 8/2009 |
| WO | WO-2009103759 A1 | 8/2009 |
| WO | WO-2009106517 A1 | 9/2009 |
| WO | WO-2009144272 A1 | 12/2009 |
| WO | WO-2010003885 A1 | 1/2010 |
| WO | WO-2010003886 A1 | 1/2010 |
| WO | WO-2010030602 A1 | 3/2010 |
| WO | WO-2010034830 A1 | 4/2010 |
| WO | 2010051079 A2 | 5/2010 |
| WO | 2010084268 A1 | 7/2010 |
| WO | WO-2010072664 A1 | 7/2010 |
| WO | WO-2010080715 A1 | 7/2010 |
| WO | WO-2010112521 A1 | 10/2010 |
| WO | WO-2011012465 A1 | 2/2011 |
| WO | WO-2011015659 A1 | 2/2011 |
| WO | WO-2011121023 A1 | 10/2011 |
| WO | WO-2012041784 A1 | 4/2012 |
| WO | WO-2012041923 A2 | 4/2012 |
| WO | WO-2012045667 A2 | 4/2012 |
| WO | 2015094945 A1 | 6/2015 |

OTHER PUBLICATIONS

PCT Patent Application No. PCT/EP2011/054910 International Search Report completed Jun. 15, 2011.

(56) References Cited

OTHER PUBLICATIONS

U.S. Appl. No. 13/583,310 Office Action dated Dec. 4, 2013.
U.S. Appl. No. 13/583,310 Office Action dated Jan. 29, 2015.
U.S. Appl. No. 13/583,310 Office Action dated Jul. 7, 2014.
U.S. Appl. No. 13/583,310 Office Action dated Sep. 11, 2015.
"Why inset®?" inset® infusion set product overview; http://web.arehive.org/web/20040906102448/http://www.infusion-setcom/DefaultaspnD=108 Printed: Jan. 9, 2008, 2 pages.

\* cited by examiner

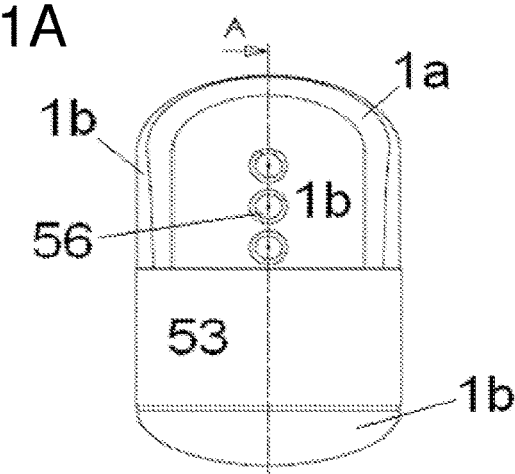
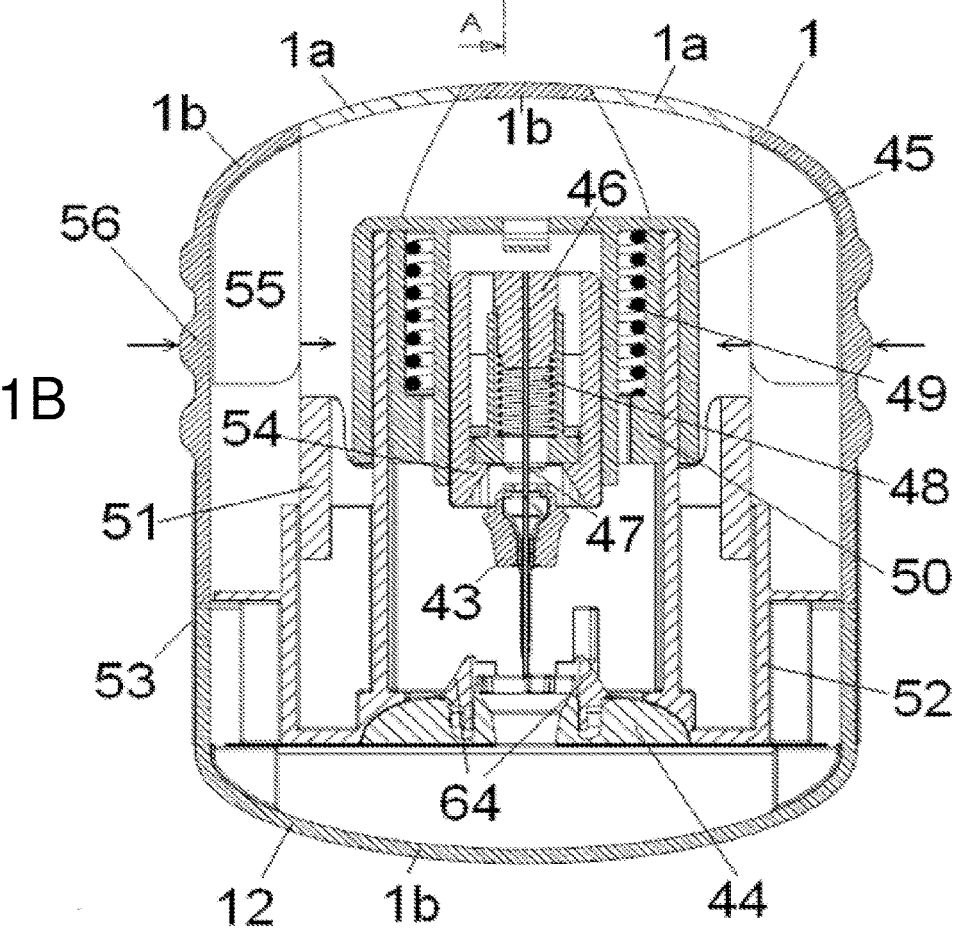

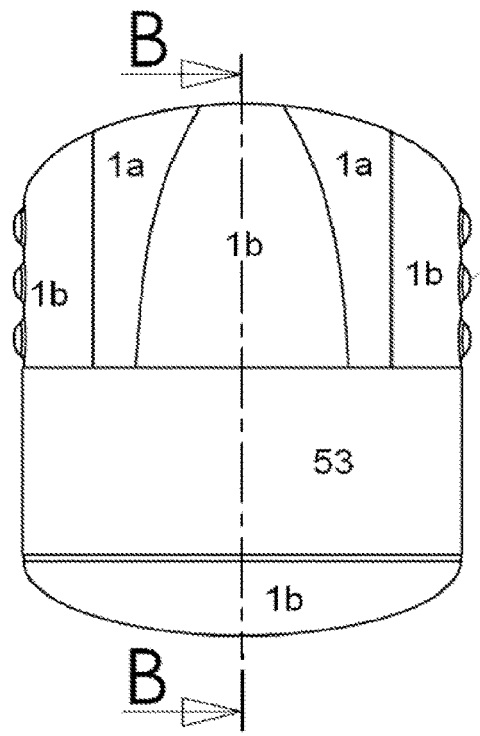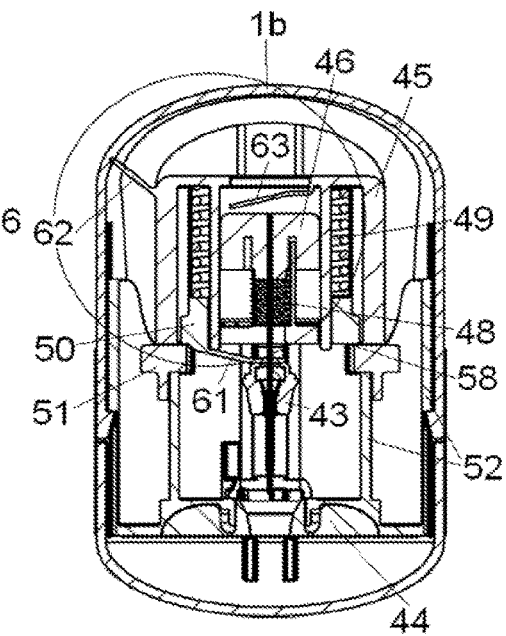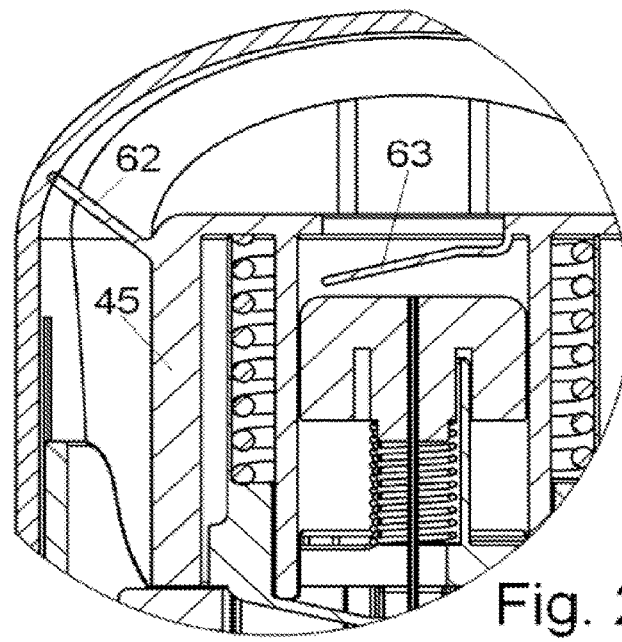
Fig. 2B
Fig. 2C
Fig. 2A

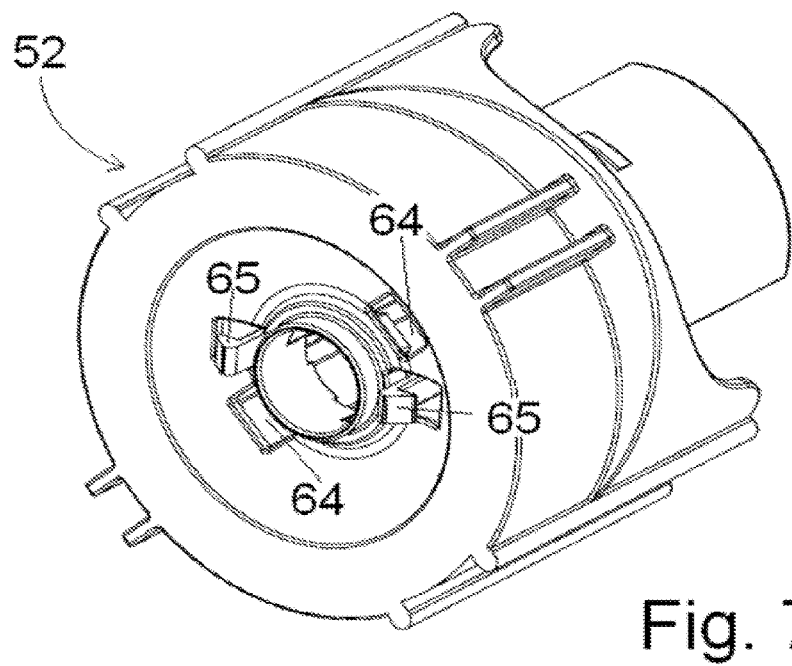
Fig. 7
Fig. 8A
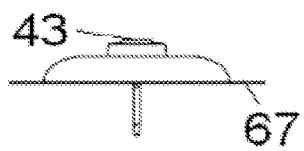
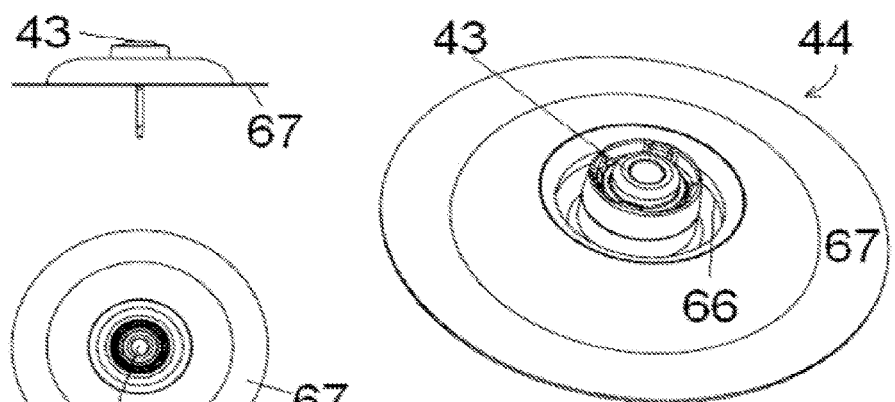
Fig. 8B
Fig. 8C

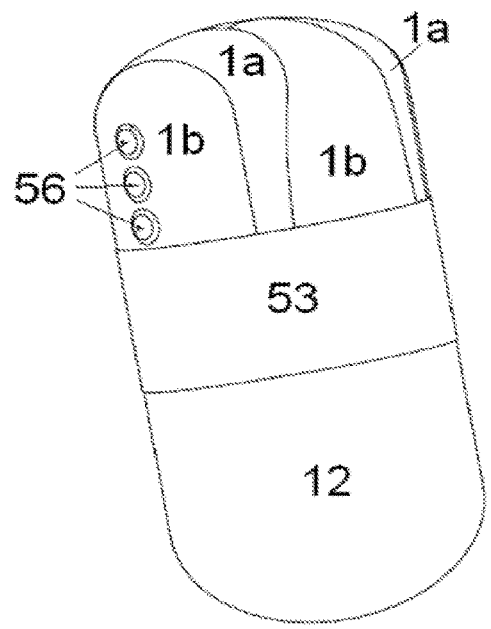
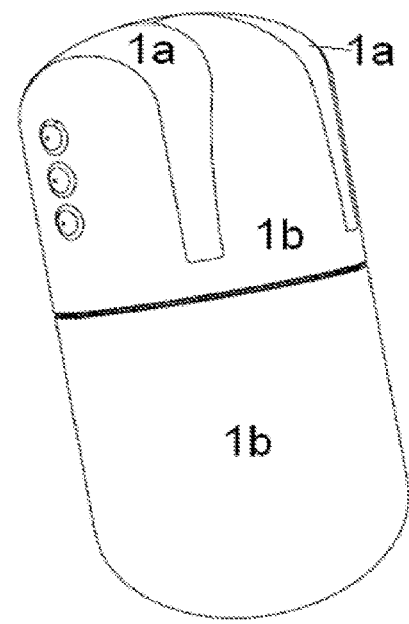
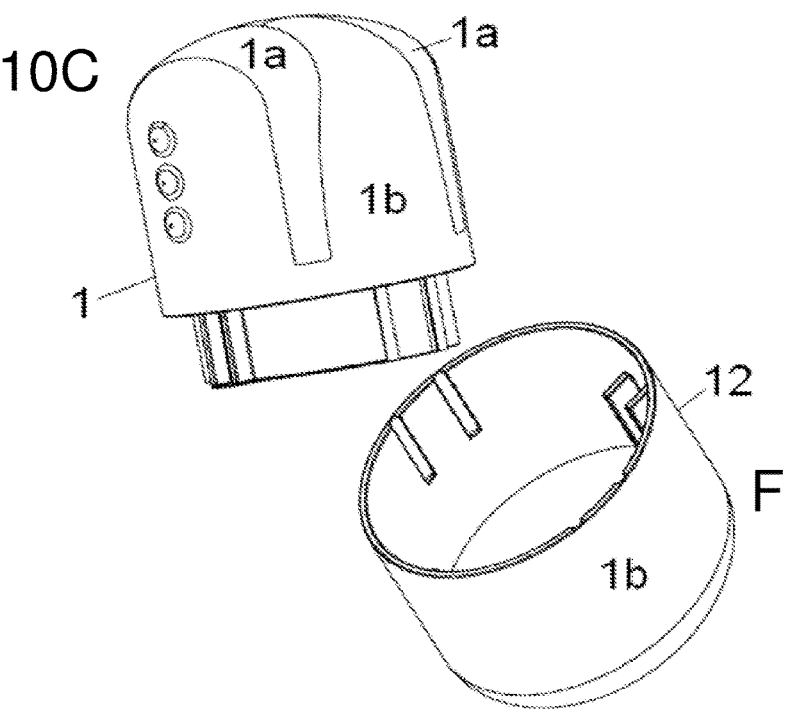

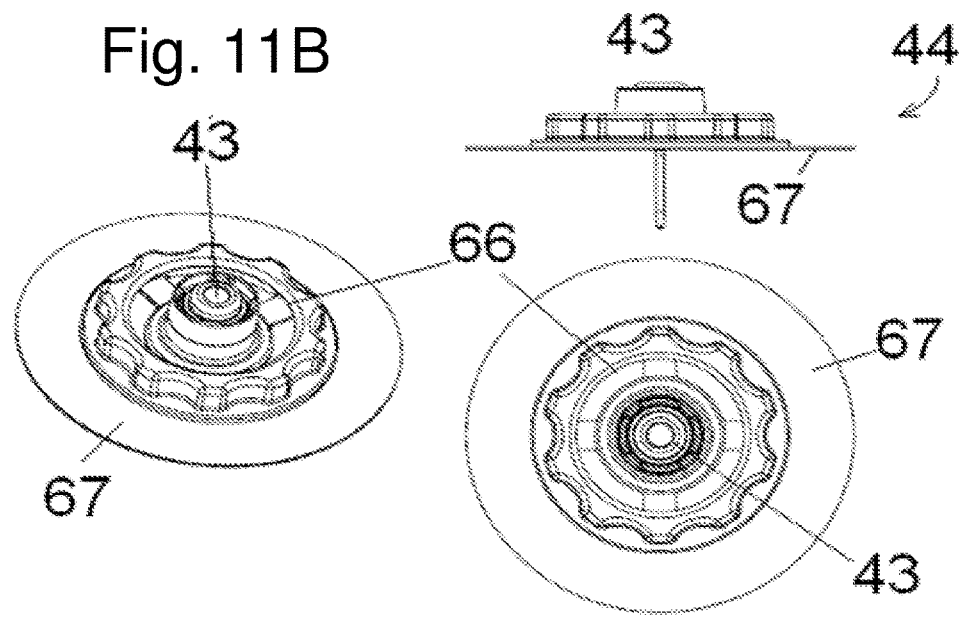

Fig. 14A
Fig. 14B
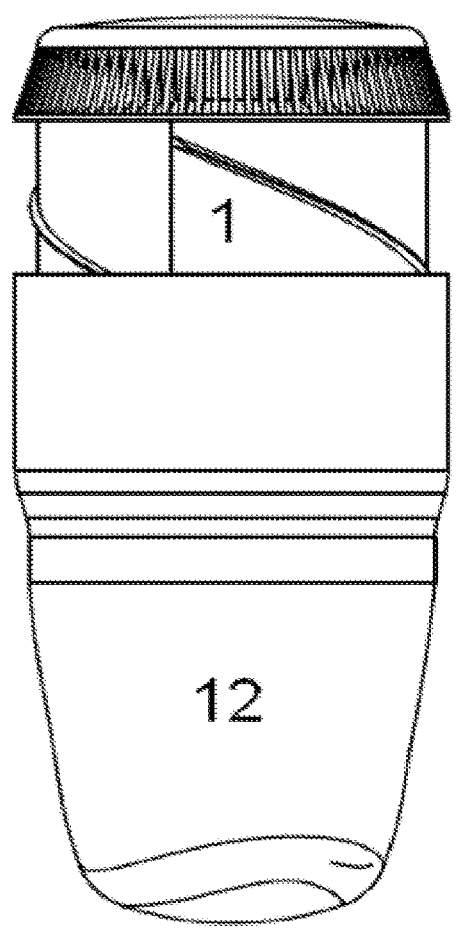
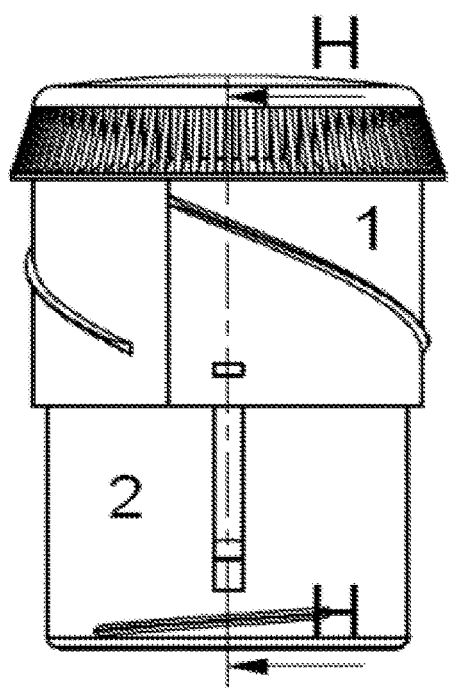

Fig. 15A
Fig. 15B
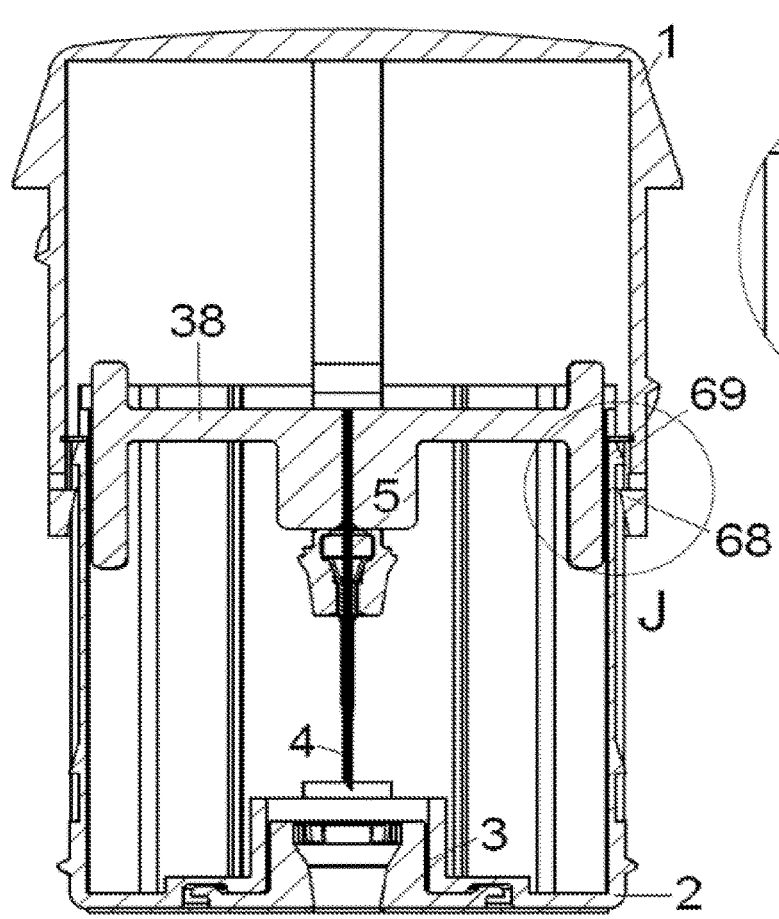
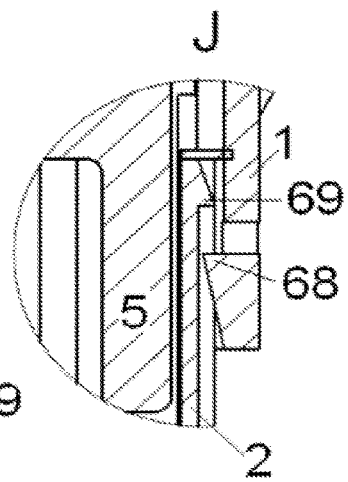

Fig. 17A
Fig. 17B
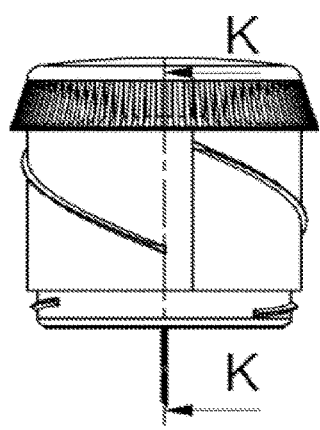
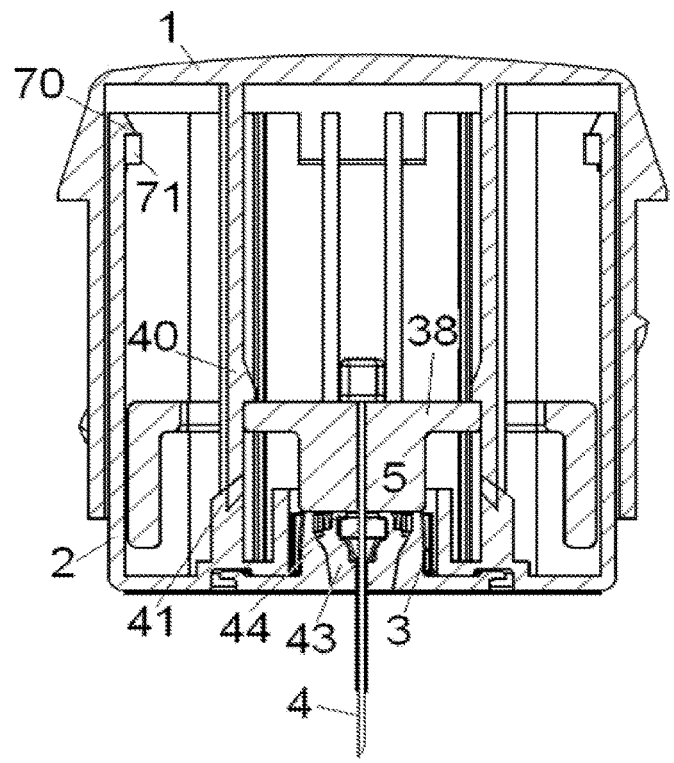

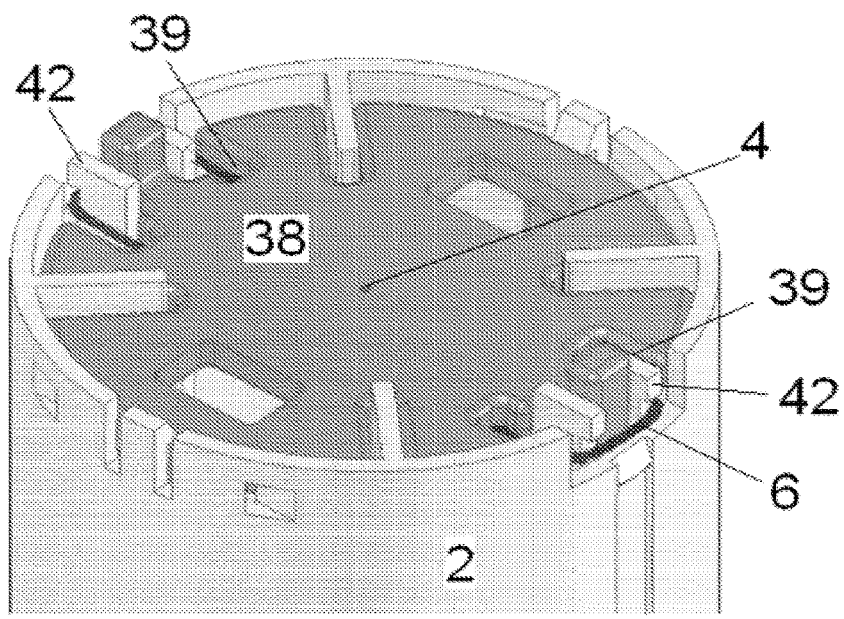
Fig. 19
Fig. 20A
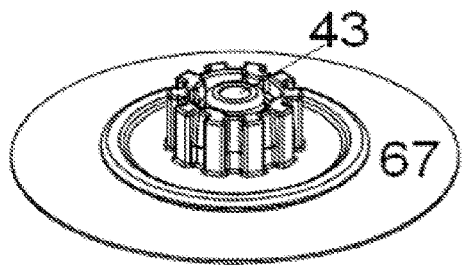
Fig. 20B
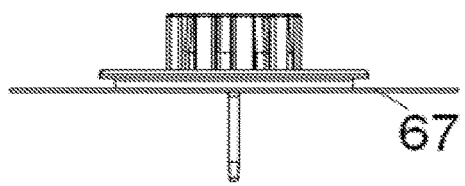

Fig. 21A
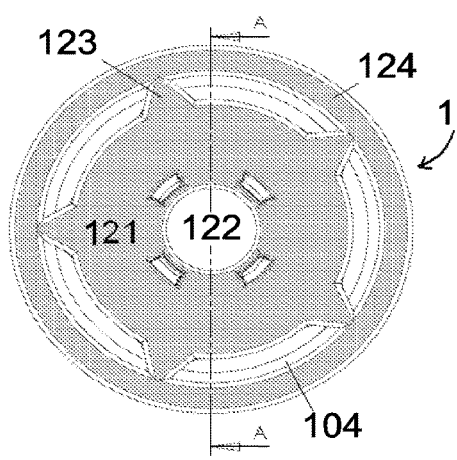
Fig. 21B
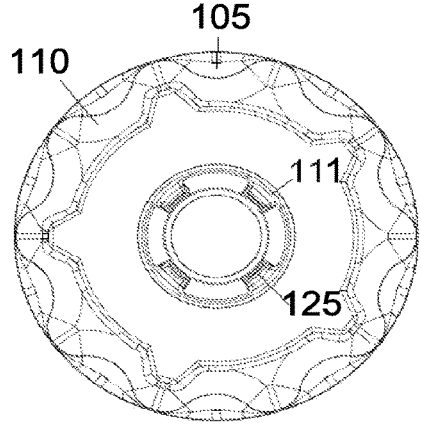
Fig. 21C
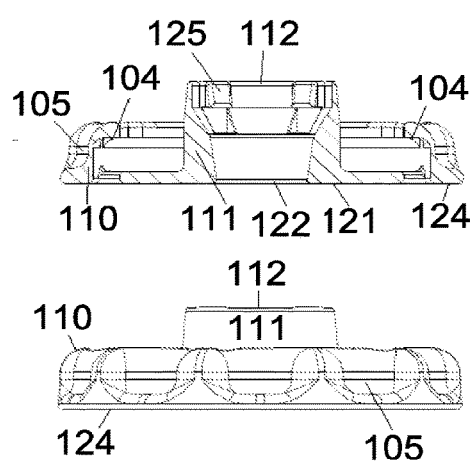
Fig. 21D
Fig. 21E
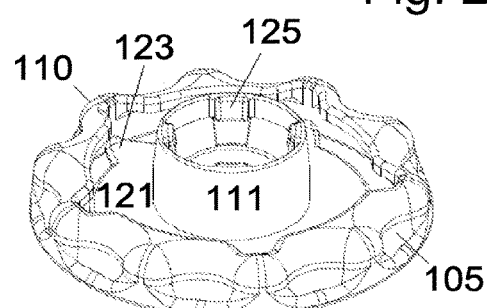

Fig. 23A
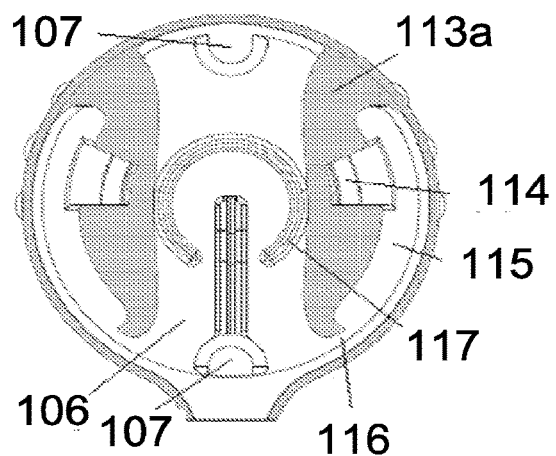
Fig. 23B
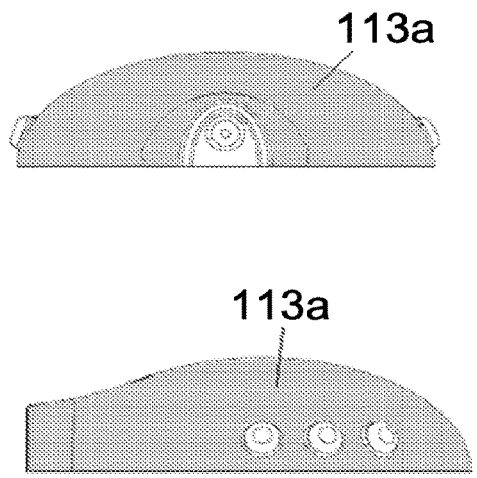
Fig. 23C
Fig. 23D
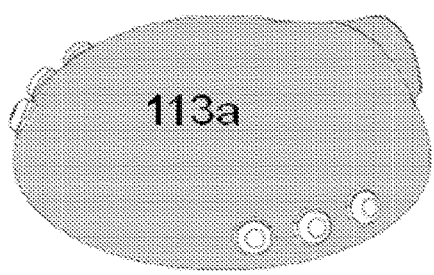
Fig. 23E
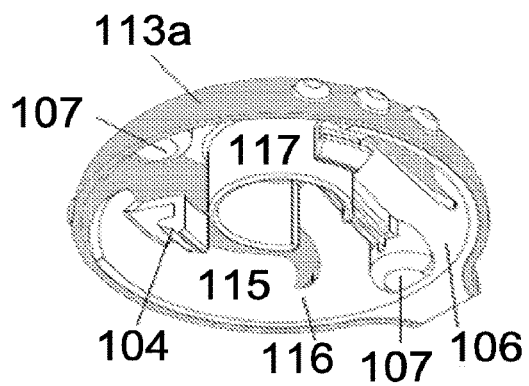

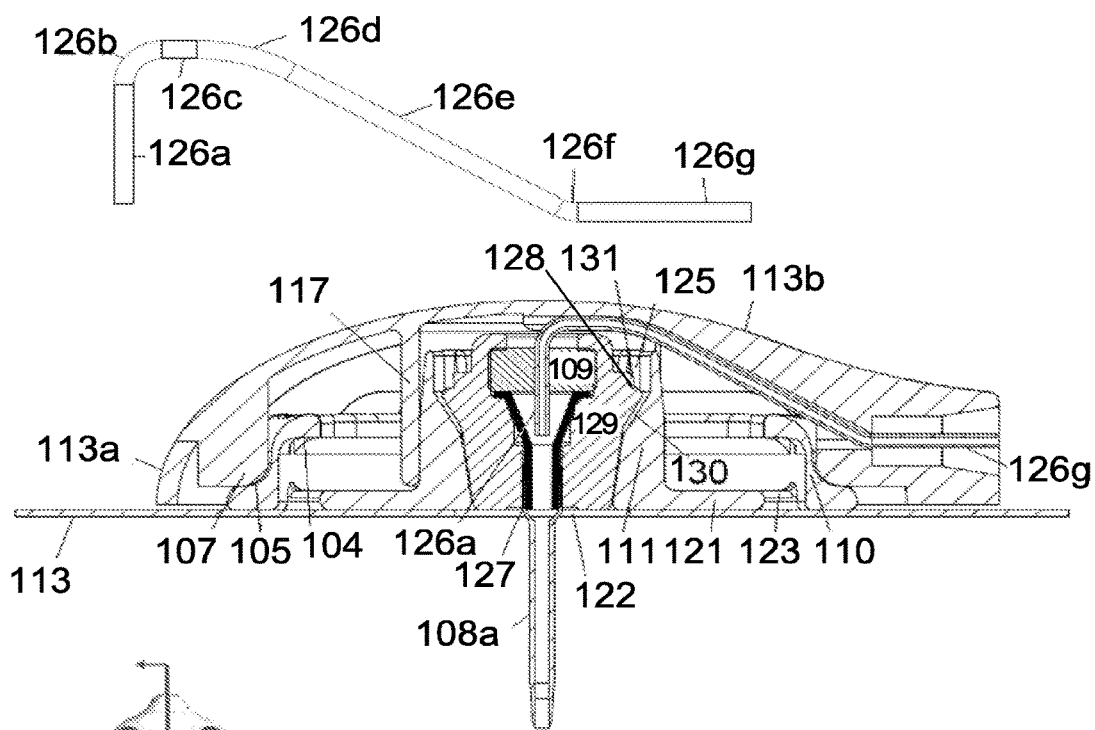
Fig. 25A
Fig. 25B
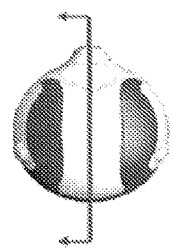
Fig. 25C

INSERTION DEVICE

CROSS-REFERENCE

This application is a continuation application of Ser. No. 13/583,310, filed Oct. 25, 2012, which issued as U.S. Pat. No. 9,415,159 on Aug. 16, 2016, which is a U.S. National Stage of PCT/EP2011/054910, filed Mar. 30, 2011, which claims the benefit of 61/318,922, filed Mar. 30, 2010 and EP Application 10158465.4, filed Mar. 30, 2010, incorporated herein by reference in its entirety and to which application we claim priority.

TECHNICAL FIELD OF THE INVENTION

The invention concerns a medical device provided with an outer part or shell and an inner functional part which inner functional part comprises a combination of units. The functional combination of units normally constitutes a device comprising a part being able to penetrate the skin of a patient i.e. a subcutaneous part such as a cannula, a sensor, an insertion needle or the like. Examples of such medical devices are inserter devices and infusion devices where each device comprises an outer part and an inner functional part.

BACKGROUND OF THE INVENTION

A lot of different medical devices are provided with a relatively hard outer shell and normally the shell is intended to protect or cover a functional part hidden inside the shell. A group of these medical devices are provided with a subcutaneous part where the outer shell during use somehow protects an insertion site e.g. during and/or after insertion of a subcutaneous part. "Protection" might e.g. imply that:
- the user or the patient is not able to see the insertion needle and/or the insertion site before, during and/or after insertion;
- the outer shell protects a subcutaneously positioned part from being moved and/or displaced by forces from the surrounding environment; and/or
- the sterility of the subcutaneous part is not compromised before, during or after insertion.

Such medical devices are e.g. known from WO 2006/062680 which document discloses an infusion set for subcutaneous delivery of an infusant. The infusion set (10) may include a base (14) removably attachable to an infusion site and a connector (12) temporarily lockable to the base (14). The connector (12) can engage the base (14) in a plurality of orientations. The connector (12) locks into the base (14) after at least partial rotation of the connector (12) about the base (14). The connector (12) may include flexible arms (16) which unlock the connector (12) from the base (14). The base (14) includes a cannula for insertion through the infusion site. The connector (12) includes tubing for passing the infusant. The infusant is subcutaneously passable from the tubing through the cannula when the connector (12) is attached to the base (14). According to this disclosure, radial locking—i.e. the features that prevents rotation of the connector relative to the base after mounting of the connector— is provided by the same parts providing the axial locking, i.e. the features that prevents the connector from being removed in a direction perpendicular to the skin surface on which it is mounted during use. According to WO 2006/062680 the radial locking means (42, 44) of the connector also provide axial locking of the connector relative to the base part as the connector is rotated into a locked position.

WO 2004/026375 discloses a catheter head with catheter drain in discrete rotational positions. The catheter head is used for introducing a fluid into an organic tissue and comprises a cannula housing (1) with a cannula (3), a connector element (2) with a fluid inlet (7), a guide and a fixing device. The guide device has several selectable discrete rotational positions for positioning the connector element relative to the cannula housing about a longitudinal axis (L) of the cannula. The connector element is positioned in a rotational position and is detachably connected to the cannula housing in the selected position by means of the fixing device.

WO 2008/065646 (Medingo Ltd) discloses an inserter device for inserting a fluid delivery device subcutaneously in order to deliver a therapeutic fluid to a patient. The inserter configuration includes automatic insertion and retraction capabilities where a trigger button (330) actuates a set of springs which fire a penetrating cartridge (150) downward into the body of the patient and retract the penetrating member after insertion. Further, the inserter includes safety mechanisms for preventing misplacement and inadvertent misfiring. According to the present application it is not necessary to provide an inserter device with complex means preventing misfiring as the spring causing insertion is not biased or loaded before insertion is intended. Actually, the user bias or loads the insertion spring just before insertion takes place.

SUMMARY OF THE INVENTION

The medical device according to the present application has a smooth outer surface and it is easy for the user to get a firm hold on the device and activate it. Activation points are placed on the outer part or shell and the activation points will normally be distinctly marked with colours or raised points or indentations. That the device has a "smooth" surface means that the surface facing the surroundings does not e.g. have any openings but appears continuous.

A medical device according to the present application comprises an outer part and an inner part which outer part provides a functional cover and which inner part comprises one or more units being protected by the functional cover during use, the outer part comprises one or more activation points on the outer surface and the activation points are connected to contact surfaces of the inner part in such a way that pressure on the activation points initiates a function of the inner part. The activation point is positioned on a section of an outer shell of the outer part constituted by a hard material and a second section of the outer shell of the outer part is constituted by a hard material and between these two portions of hard material, the outer shell comprises a third section constituted by a soft and flexible material.

According to one or more embodiments the outer part constitute a housing, which housing provides a rounded and continuous surface without any openings providing access to the inner functional parts, and where the housing has two opposite side parts or "arms" and comprises two wedges of softer material.

According to one or more embodiments the outer part comprises at least two pressure points positioned at opposite positions on the outer shell and therefore the shell comprises at least two separated sections of soft material.

According to one or more embodiments the sections of hard material is constituted of ABS (Acrylonitrile butadiene styrene).

According to one or more embodiments the sections of soft material is constituted of TPE (Thermoplastic Elastomer).

According to one or more embodiments the hard material constitutes a web or skeleton and the soft material is placed between a central part of hard material and a side part of hard material which side part is provided with activation points.

According to this embodiment the housing can comprise two opposite side parts or "arms" and therefore comprises two wedges of softer material.

According to one or more embodiments the medical device is an inserter device and the outer part constitutes a housing at least partly covering the inner functional part which further comprises a cover which is slidably attached to the housing and has at least one retracted and one forward position relative to the housing. According to these one or more embodiments, the inserter device can comprise a first spring and a second spring. The first spring can be releasably attached to the upper end of the cover which is slidably attached to the housing at a first end and at the second end it is indirectly connected to the housing in such a way that the second end of the first spring can be displaced by rotating the housing relative to the cover. The first spring can comprise at least one elastically mounted arm which arm at the upper end, i.e. the distal end compared to the patients skin during insertion, is provided with an outward hook securing the arm to the cover by catching around and upper edge of the cover.

According to one or more embodiments the medical device is an inserter device and the inner part comprises a first part and a second part, which first part is slidably attached to the second part and has at least one retracted and one forward position relative to the second part.

According to one or more embodiments, the inserter device comprises a first spring and a second spring. According to these one or more embodiments, the inner part further comprises an inner lid, and the first spring rest against a surface of the inner lid at a first end and at the second end the first spring rests against a surface of the second part in such a way that the first spring is in a loaded position when the first part is in the retracted position and in an unloaded position when the first part is in the forward position.

According to one or more embodiments the first spring can be displaced from the loaded position to the unloaded position by pressing the activation point towards each other.

According to one or more embodiments, the inner part further comprises a third part, which third part is slidably attached to the second part and has at least one retracted and one forward position relative to the second part. According to these one or more embodiments, the second spring rest against a surface of the third part at a first end and at the second end the first spring rests against a surface of the second part in such a way that the second spring is in a loaded position when the third part is in the forward position and in an unloaded position when the third part is in the retracted position. The second spring is automatically displaced from the loaded position to the unloaded position subsequent to the displacement of the first spring prompt by pressing the activation point towards each other.

According to one or more embodiments an inclined surface of the housing through contact with a surface of the first spring or of a part in a fixed connection with the first spring forces the second end of the first spring away from upper end of the cover.

According to one or more embodiments the first spring can be releasably attached to the upper end of the cover at a first end and at the second end it is indirectly connected to the housing in such a way that the second end of the first spring can be displaced by pressing the housing and the cover towards each other along the longitudinal axis of the two parts. The first spring can at the upper end be provided with an outward hook securing the upper end of the first spring to the cover by catching around and upper edge of the cover. According to these embodiments a central part of the housing through contact with a surface of the second end of the first spring or of a part in a fixed connection with the second end of the first spring forces the second end of the first spring away from upper end of the cover.

According to one or more embodiments the medical device is an infusion device and the outer part constitute the outer shell of a connector part and the inner part constitutes an infusion part comprising a subcutaneously positioned cannula and/or sensor during use.

According to embodiments related to infusion devices or similar devices to be left on a patients skin the outer part fully covers the site when mounted on the site.

That the site is fully covered means that when the site is mounted on a patients skin and the connector part is attached to the site, then it is not possible to see any part of the site from above i.e. from a view perpendicular to the patients skin.

According to one or more embodiments the outer surface of the outer part is constituted by a single flexible material and a structure of hard material is connected to the inner surface i.e. the surface facing the site i.e. the hard material is hidden behind/below the outer flexible material.

According to one or more embodiments the outer surface of the outer part is constituted by one or more areas of flexible material combined with one or more areas of hard material i.e. both the soft and the hard material forms part of the outer and the inner surface of the cover.

According to one or more embodiments, the actuator means is connected to or being a part of the outer part or cover.

According to one or more embodiments the site has a surface directly or indirectly attached to the skin of the patient during use and this surface comprises at least two separated parts where the first part is connected to the subcutaneous part during use and secure this part to the patients skin and the second part is surrounding the first part and secures the vertical positioning means of the site to the skin of the patient. The separation or flexible connection between the first and the second part prevents movements from the second part from being transferred to the first part holding the subcutaneous part.

According to one or more embodiments the first part is connected to the second part via two or more strings of e.g. hard material.

According to one or more embodiments the horizontal positioning parts comprise one or more protruding parts placed along a straight line passing through the center of the connector and the actuating means are placed on one or both sides of the straight line. E.g. the connector part has one or two horizontal positioning parts and at least one of the horizontal positioning part(s) is/are placed at the periphery of the connector part.

According to one or more embodiments the positioning means of the site comprise at least two openings where at least one opening correspond(s) to a protruding part on the connector part when the connector part is placed in a use position. E.g. the positioning means of the site comprise at least two openings where two or more openings correspond to two or more protruding part on the connector part when the connector part is placed in a use position.

According to one or more embodiments the positioning means of the site comprise two to ten openings corresponding to two to ten protruding parts on the connector part when the connector part is placed in a use position.

According to one or more embodiment the site has a subcutaneous part when positioned on the patients skin or has means for attaching a subcutaneous part after positioning the site on the patients skin.

According to one or more embodiment the attachment means of the site comprises an increase or a decrease in a cross-sectional dimension providing an inward or outward step in a vertical profile. E.g. the attachment means comprise an outward rim at an outer vertical surface or an inward rim at an inner vertical surface.

According to one or more embodiments the means for attachment of the connector part comprises actuation means in the form of at least one arm placed along the outer edge of the connector part which arm is fastened to the connector part at one end and can be pivoted around this fastening point, the arm is provided with retaining means configured to prevent vertical movements of the connector part relative to the site.

According to one or more embodiments the means for attachment of the connector part comprises actuation means in the form of two oppositely positioned arms which arms each are pivotally attached at one end and each arm is provided with retaining means and the distance between the retaining means on each arm can be varied due to the pivotal movement of the two arms.

According to one or more embodiments the connector part comprises a connector needle in the form of a tubular element to be inserted through a septum of the site. According to this embodiment the connector part can be provided with guiding means adapted to guide the tubular element through a penetrable part of the site in a vertical direction.

According to one or more embodiments the device comprises a leakage indication system comprising leakage indication means adapted to provide a colour change upon leakage of a fluid, the indication means being provided on a surface of the site near the insertion site, and being visible i.e. inspectable upon use. The leakage indication system can comprise a reference marker indicating the visual change to be expected upon leakage.

According to one or more embodiments the device comprises a subcutaneous part comprising a coloured or contrast-enhanced cannula, and the site comprises a transparent area arranged near the insertion site, said transparent area being adapted to allow visible detection of misplacement of the cannula during use.

BRIEF DESCRIPTION OF THE DRAWINGS

A detailed description of embodiments of the current invention will be made with reference to the accompanying figures, wherein like numerals designate corresponding parts in different figures.

FIGS. 1A-1B shows an embodiment of an inserter device. FIG. 1B shows a cut-through view along line A-A of an embodiment of an inserter device FIG. 1A shows where the cut is made.

FIGS. 2A-2C shows a cut-through view along line B-B of the same embodiment of an inserter device as FIGS. 1A-1B but the cut-through view is from an angle perpendicular to the angle shown in FIG. 1A. FIG. 2A shows an enlargement of the encircled part marked "C" of FIG. 2C.

FIG. 7 shows an embodiment of an internal base which can be used with the embodiments of the inserter device shown in FIGS. 1A-1B, 2A-2C, 3-4, 5A-5B, and 6.

FIGS. 8A-8C shows an embodiment of a base in the form of a port site which can be used with the embodiment of the inserter device shown in FIGS. 1A-1B, 2A-2C, 3, 4, 5A-5B, and 6.

FIGS. 10A-10D shows the inserter device in a before-use-state where a tamperproof band has not yet been removed, in a state where the tamperproof band has been removed and the device is ready to be used, and in a state where a lid has been removed and the inserter is ready to be placed against the skin of the patient.

FIGS. 11A-11C show an embodiment of an infusion site which can be positioned with the inserter of FIG. 9.

FIG. 13B shows a cut-through view along the line G-G in FIG. 13A.

FIGS. 14A-14B shows the inserter device of FIGS. 13A-13B in a side view in a pre-loaded state.

FIGS. 15A-15B and FIGS. 16A-16B show cut-through views of the inserter device in the preloaded state of FIGS. 14A-14B; FIG. 15A shows a cut-through view along the line H-H of FIG. 14B and FIG. 16B shows a cut-through view along the line Q-Q in FIG. 16A.

FIGS. 17A-17B shows the embodiment of the inserter device in a loaded state where the primary spring is as extended as it will be during operation of the inserter device and the insertion needle is fully inserted. FIG. 17B shows a cut-through view along the line K-K in FIG. 17A.

FIG. 18B shows a cut-through view along the line O-O in FIG. 18A.

FIG. 19 shows a possible position of a primary spring in the form of an elastic band such as a rubber band used with the embodiment of the inserter device.

FIGS. 20A-20B shows a medical device comprising a subcutaneous part and an infusion site.

FIGS. 21A-21E show a fourth embodiment of a medial device comprising a site in the form of an infusion site which can be combined with a subcutaneous part.

FIGS. 23A-23E show an embodiment of a connector part that can be used together with the sites of FIGS. 21A-21E.

FIG. 25A shows a side view of a connector needle, FIG. 25B shows a cut-through view of a site on which a connector part as shown in FIGS. 22A-22E is mounted, and FIG. 25C shows a line along which the cut-through view of FIG. 25B is taken.

DETAILED DESCRIPTION OF THE INVENTION

Figure 3:
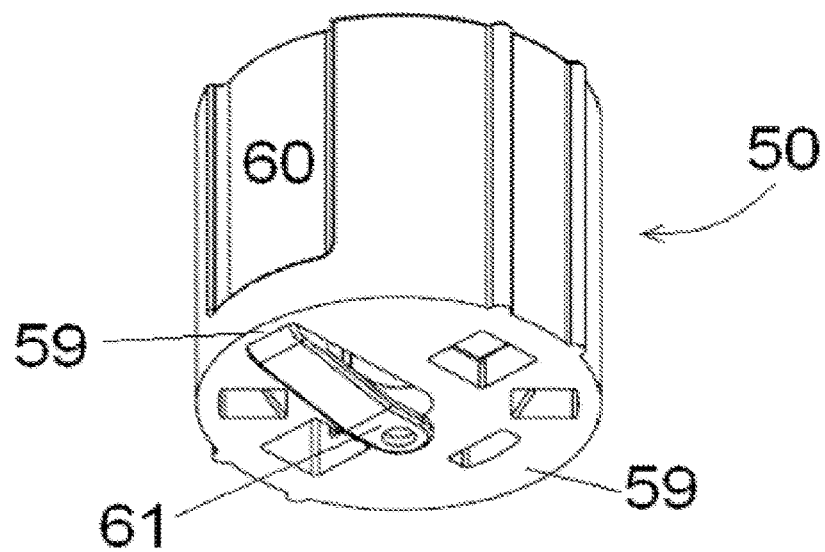
FIG. 3 shows an enlargement of an embodiment of an insertion part.

FIGS. 1A-1B shows a first embodiment of a medical device being an inserter device. The embodiment of the inserter device has automatic insertion and automatic retraction of an introducer needle 47 and is used for placing a base part 44 combined with a subcutaneous part 43 subcutaneously in a patient. The embodiment comprises an outer part which comprises a housing 1 constituted by sections of a soft material 1a and sections of a hard material 1b. The housing 1 also comprises position indicators 56 for activation and protruding parts 55 situated on the inner surface of the housing 1. The inner functional part of the inserter device comprises:

an inner lid 45 provided with a plastic spring 62 and an elastic unit 63 (seen more clearly in FIG. 2A);
a retraction part 46 provided with inward hooks 54;
an introducer needle 47 attached to the retraction part 46;
a retraction spring 48 placed between the retraction part 46 and an insertion part 50 (see also FIG. 3), wherein the insertion part 50 is provided with downward facing contact surfaces 59, grooves 60 in the outer surfaces and means 61 for releasing the subcutaneous part 43;
an insertion spring 49 placed between the inner lid 45 and the insertion part 50;
a release part 51 (see also FIG. 4) provided with push positions 57 and protruding parts 58; and
an internal base 52 to which the base 44 is attached before and during insertion of the subcutaneous part 43.

Before use the device is provided with a lid 12 and a tamperproof band 53. All of the pieces are normally made of moulded plastic except e.g. the insertion needle 47 which might be made of metal.

When the user has prepared the inserter device for insertion by removing the lid 12, the user places the device against the skin of the patient whether this might be the user himself or a second person. According to the shown embodiment the base 44 is placed in a position at the proximal end of the internal base 52 and does not form an integral part with the subcutaneously part 43. Normally the base 44 has an adhesive surface, which can be exposed by removing the lid 12. The adhesive surface is used to attach the base 44 releasably to the patients skin. The adhesive surface could be exposed automatically upon removal of the lid 12 or it could be exposed manually e.g. by removing a release paper from the adhesive surface before use. When the adhesive surface is exposed the end of the inserter device comprising the base 44 is pushed against the skin of the patient, and then the trigger is activated. The trigger according to the shown embodiment is activated by pressing two opposite flexible points at the top end of the housing 1.

In more detail, FIG. 1B shows a cut-through view along line A-A of an embodiment of an inserter device (FIG. 1A shows where the cut is made). The inserter device is used for insertion of a subcutaneous part 43 into a base which subcutaneous part 43 in FIG. 1B is illustrated as a cannula part and which base 44 in FIG. 1B is illustrated as a port site i.e. a site which can be used for injecting portions of medication over a period of normally up to 3 days. The device is shown in a pre-use state.

Before use, the housing 1 is closed with a lid 12 and a tamperproof band 53 is placed along the separation line between the housing 1 and the lid 12. The tamperproof band 53 can be penetrated by sterilizing gas and is placed around the device before sterilization. An intact tamperproof band 53 thus ensures that the housing 1 has not been separated from the lid 12 after sterilization of the device, i.e. correct placement of the tamperproof band 53 indicates to the user that the disposable inserter device is sterile and ready for use.

The inserter device comprises an inner lid 45, a retraction part 46 to which an introducer needle 47 is attached unreleasably, a retraction spring 48, an insertion spring 49, an insertion part 50, a release part 51 and an internal base 52.

The internal base 52 provides the skeleton for the inserter device and all other parts are connected to the internal base 52. The inner lid 45 is locked to the internal base 52 and therefore these two parts are stationary relative to each other through all actions of the inserter device. One end of the insertion spring 49—the upper end—rests against a surface of the inner lid 45. The opposite second end of the insertion spring 49—the lower end—rests against an upward facing surface of the insertion part 50. Before insertion of the subcutaneous part 43, the insertion part 50 is placed at the upper half i.e. at the closed end of the inner lid 45 and the insertion spring 49 is loaded. Normally, the insertion device is brought to this step during the manufacturing procedure. A downward facing surface of the insertion part 50 rests against one or more upward facing surfaces of the release part 51, this contact prevents the insertion part 50 from being pushed downwards by the insertion spring 49 before activating the device. The release part 51 is also stationary relative to the internal base 52, at least the release part 51 does not move relative to the internal base 52 along the direction of insertion.

Before use the base 44 is attached to the internal base 52 and the internal base 52 is therefore provided with a corresponding position for receiving such a base 44. The lower surface of the base 44 i.e. the surface facing the patient when the base 44 is attached to a patients skin, is attached unreleasably to an adhesive e.g. the base 44 is welded to a patch provided with an adhesive lower side. The adhesive surface will normally be covered by a release paper or another protective cover protecting the adhesive surface and ensuring that the adhesive surface is as adhesive as intended by the manufacturer. The release paper might be attached to the lid 12; this will cause the release paper to be removed simultaneously with the lid 12 thereby saving the user a step during the positioning procedure.

In FIG. 1B the subcutaneous part 43 is attached to the retraction part 46. The subcutaneous part 43 is positioned on the insertion needle 47 and is kept in position due to the friction between the insertion needle 47 and the soft contact parts of the subcutaneous part 43 such as a cannula, respectively.

The retraction part 46 is at this state attached to the insertion part 50 by two or more inward hooks 54 at the lower end of the retraction part 46. As the retraction spring 48 pushes the retraction part 46 upward i.e. opposite the direction of insertion, the inward hooks 54 lock the retraction part 46 to the insertion part 50 as the inward hooks 54 prevent the retraction part 46 from moving in the direction opposite the direction of insertion.

The embodiment in FIGS. 1A-1B is provided with a safety function preventing unintended activation of the insertion device. When the lid 12 is in the shown closed position, the housing 1 cannot move relative to the internal base 52. In order to be able to activate the insertion device it will be necessary to push the housing down until inner activation means having the form of two oppositely positioned protruding parts 55 attached to or being part of the inner surface of the housing are placed opposite flexible parts of the release part 51. In the state shown in FIGS. 14A-14B it is not possible to activate the insertion as the protruding parts 55 is not correctly positioned opposite the release part 51, arrows indicate how the protruding parts are moved during activation. A spring 62 is normally placed between an upper part of the inner lid 45 and an inner surface of the housing 1 to keep the housing 1 pushed away from the top of the inner lid 45, this will necessitate an action from the user when the device is to be activated namely pushing the housing 1 towards the inner lid 45 which will force the user to push the housing 1 in direction of the patients skin just before insertion is activated. This is an easy performed and a natural thing to do for the user, especially if the user is the patient him/her self.

The lower wall of the internal base 52 provides an almost complete cover for the parts hidden inside the housing 1. The lower wall of the internal base 52 is only provided with a central opening where through the subcutaneous part 43 can pass when inserted. Also, the lower wall of the internal base 52 can have e.g. smaller openings where through attachment means might protrude. The openings in the lower wall of the internal base 52 is so small that it will not be possible to put a finger through the opening an e.g. get in contact with the used introducer needle 47.

The outer shell of the embodiment of the housing 1 shown in FIGS. 14A-14B provides a rounded and continuous surface without any openings providing access to the inner functional parts and is a composite of one or more materials as sections of a hard material is combined with one or more sections of a soft and/or elastic material. That the material is "soft and/or elastic" means that it is more flexible and/or elastic than the hard material and that it is possible to reduce a dimension of the material due to pressure provided by the user.

The sections of soft material are referred to as 1a and the sections of hard material are referred to as 1b. According to one embodiment the sections of hard material can be constituted of ABS (acrylonitrile butadiene styrene) and the sections of soft material can be constituted of TPE (thermoplastic elastomer) where the ABS part provides as a hard shell or skeleton including, e.g. the protruding parts 55, on the inner side surface of the housing 1 and knobs, i.e. positioning indicators 56, on the outer surface of the housing 1. According to the embodiment the softer material is covering the gab that makes it possible to push the activation means together. According to the present embodiment a wedge of soft material is placed between a central part of hard material and a side part of hard material which side part is provided with position indicators 56 for activation. The shown embodiment has two opposite side parts or "arms" and therefore comprises two wedges of softer material. When the user squeezes the two "arms" together or alternatively squeezes one arm towards the hard central part, the section constituting the softer material of the wedges is reduced in width, i.e. either by folding or by pressing.

The lid 12 will normally be made of a hard non-flexible material.

The shown embodiment is very easy to handle, although the user has not been introduced to the functioning of the device it will be almost impossible to do anything wrong. Also, there is no risk of getting in contact with the introducer needle after positioning of the subcutaneous device, since the introducer needle 47 is brought into a retracted position inside the housing 1. The patient will not be able to see the introducer needle 47 or touch it. As the insertion springs 49 is unloaded after insertion of the subcutaneous part 43 there will be no risk of repeating the injection procedure.

FIG. 2C shows a cut-through view along line B-B of the same embodiment of an inserter device as FIGS. 1A-1B. However, the cut-through view is from an angle perpendicular to the angle shown in FIG. 1. FIG. 2A shows an enlargement of the encircled part marked "C" of FIG. 2C.

From the cut-through view along line B-B, it is possible to see that the internal base 52 rests against upward surfaces formed from the inner surfaces of the housing 1 and this contact assures that the internal base 52 is locked relative to the housing 1, or more precisely, the housing 1 can move from a resting position in the direction of insertion relative to the internal base 52 and return to the resting position, but the housing 1 can not be moved from the resting position in a direction opposite of insertion or in any other direction. The resting position is a position where the housing 1 is stationary when not influenced by a force coming from outside the inserter device.

Also, it is possible to see a plastic spring 62 placed between the outer surface of the inner lid 45 and the inner surface of the housing 1. This plastic spring 62 provides a back pressure when the housing 1 is pressed towards the internal base 52 and ensures that the housing 1 is kept in place. The plastic spring 62 is ac-cording to this embodiment a flat spring made of same material as the inner lid 45, the plastic spring 62 can be a part of the inner lid 45.

The inserter device is further provided with an elastic unit 63 between the inner lid 45 and the retraction part 46 which elastic unit 63 reduces sound when the retraction takes place. In the shown embodiment the elastic unit 63 has the form of a flat spring attached to the inner lid 45 at one end and touching the retraction part 46 with the other end when the retraction part 46 is forced towards the inner lid 45 by the retraction spring 48. The elastic unit 63 might also be a part of the inner lid 45 and therefore made of same material.

Figure 4:
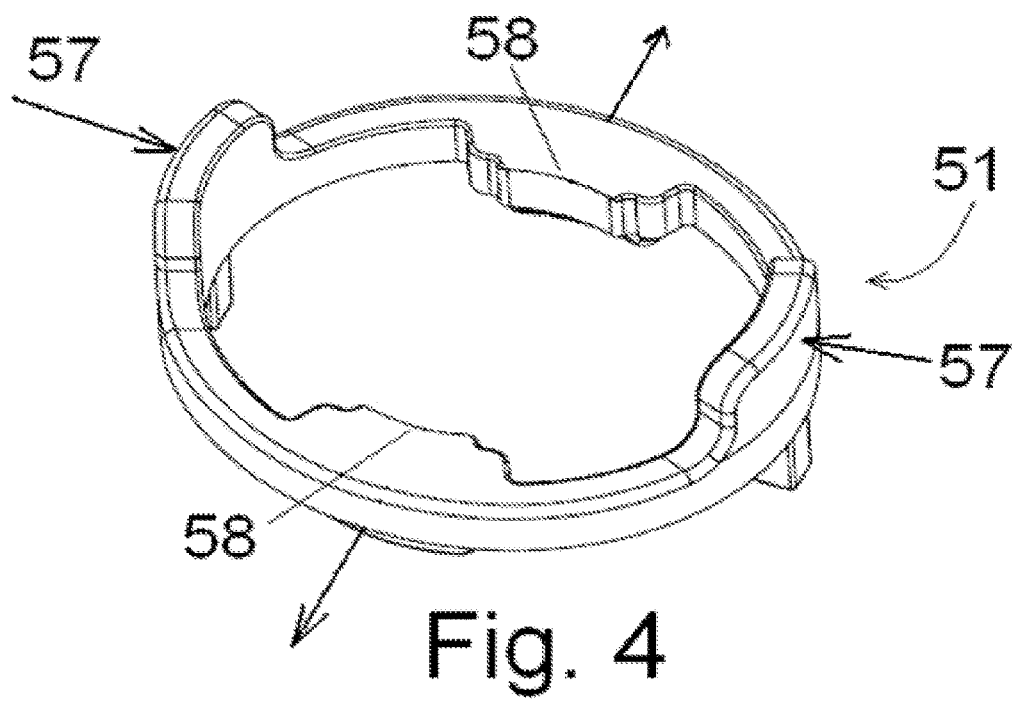
FIG. 4 shows an enlargement of an embodiment of a release part.
Figure 5:
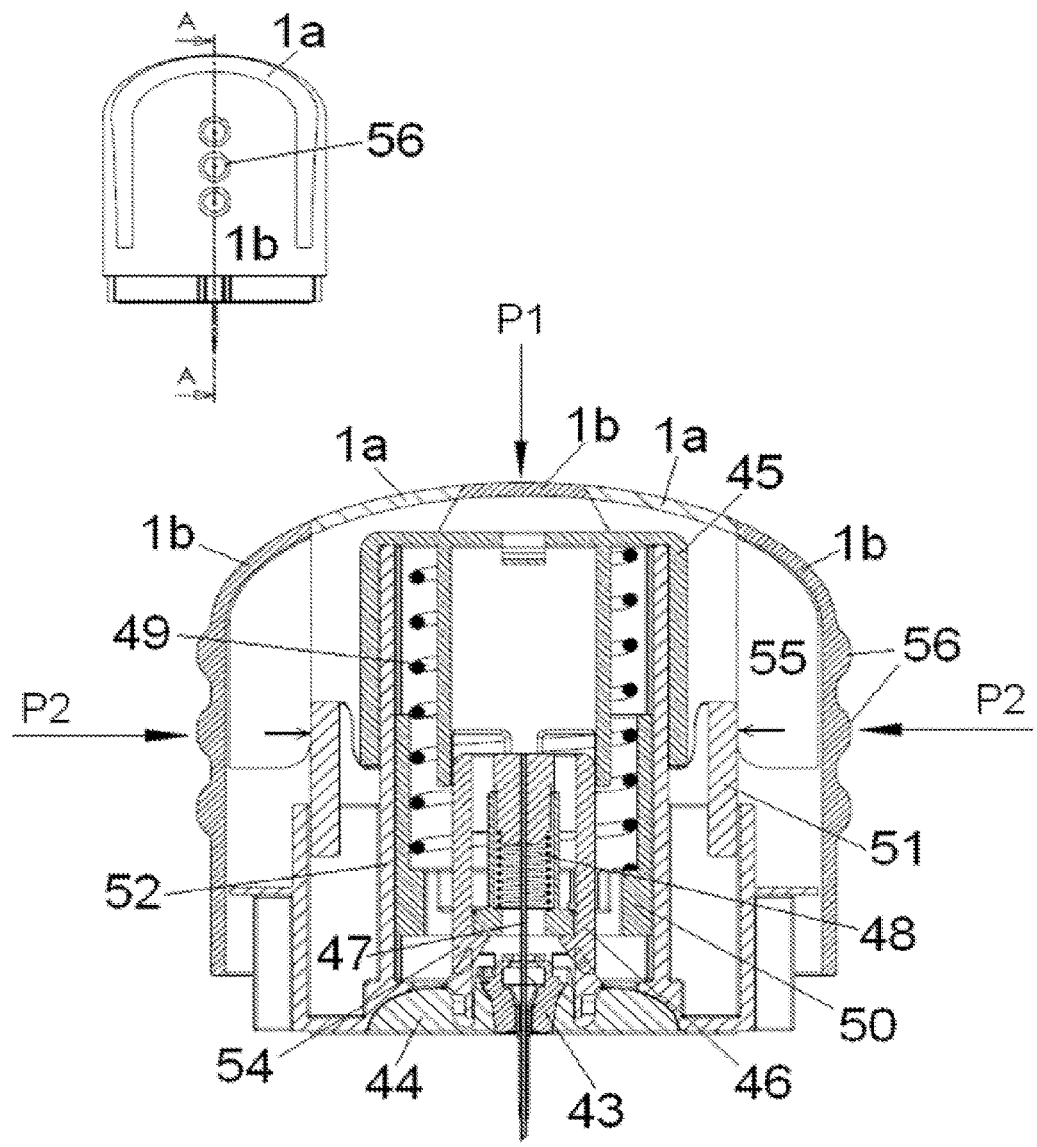
FIGS. 5A-5B shows a cut-through view along line A-A of the same embodiment as shown in FIGS. 1A-1B and 2A-2C in a state where it has been activated and a subcutaneous part has been subcutaneously inserted while the introducer needle has not yet been retracted.

FIGS. 5A-5B shows a cut-through view along line A-A of the same embodiment of the inserter device as shown in FIGS. 1A-1B and 2A-2C. The cut-through view along line A-A in FIG. 5A is from the same angle as the cut-through view in FIG. 1B, however the device is in here shown in a state where it has been activated, thus the subcutaneous part 43 has been subcutaneously inserted but the introducer needle 47 has not yet been retracted. FIG. 3 shows an enlargement of an embodiment of an insertion part 50 and FIG. 4 shows an enlargement of an embodiment of a release part 51.

At the state displayed in FIGS. 5A-5B, the insertion spring 49 has been released. The inserter device was brought into this activated state by a user by first removing the lid 12, then releasing the safety feature by pressing on top of the housing 1 as indicated by the arrow P1, and subsequently placing the open end of the inserter device against the patient's skin. At this position an adhesive surface of the base 44 is normally attached to the patient's skin. When the housing 1 is pushed down in the direction of the arrow P1, i.e. in the insertion direction, the housing 1 will move forward relative to the internal base 52 until it meets a stop. When the housing 1 cannot move further forward/down, the protruding parts 55 of the housing are positioned opposite elastic parts of the release part 51.

In a state where the release part 51 is not influenced by external forces, the release part 51 is a circular or oval elastic ring having at least one push position 57. In the shown embodiment see more clearly in FIG. 4, the release part 51 has two push positions 57. When activating the release part 51, the release part 51 is forced into another shape, i.e. an oval shape, as the protruding parts 55 of the housing 1 is pressed towards the push positions 57 of the release part 51. When activated the release part 51 looses it grip in the insertion part 50 as the release part 51 is extended in one direction which results in that the dimension of the release part 51 is reduced in another direction. The insertion part 50 rests on, i.e. is in contact with, the inward protruding parts 58 of the release part 51. The downward facing surfaces of the insertion part 50 which are in contact with upward surfaces of the protruding parts 58 before activation of the insertion device is indicated by ref. no. 59 in FIG. 3 and FIGS. 5A-5B.

The insertion part 50 is provided with grooves 60 in the outer surface and the protruding parts 58 of the release part 51 can move in or slide along the surface of these grooves 60 so that the contact between the protruding parts 58 and the outer surface of the insertion part 50 does not prevent the movement of the insertion part 50 in the direction of insertion.

Also, the insertion part 50 is provided with means 61 for releasing the subcutaneous part 43 from the insertion part 50. These means 61 for releasing the subcutaneous part 43 can have the form of a distance piece which assures that the subcutaneous part 43 is pushed down into the opening of the base 44 with such a force that the subcutaneous part 43 can get past or get in contact with the locking mechanism inside the opening of the base 44. In the embodiment of FIGS. 5A-5B, the means 61 for releasing comprise a flat spring placed between the lower surface of the insertion part 50 and the upper surface of the subcutaneous part 43. The flat spring is attached to or is a part of the insertion at one end. As the insertion part 50 is pushed down towards the base 44 by the insertion spring 49, the flat spring 61 will be loaded when the insertion part 50 gets close enough to the base 44. The flat spring 61 will then exercise a pressure on the subcutaneous part 43 which will provide that the subcutaneous part 43 is locked inside the opening of the base 44.

At the state displayed in FIGS. 5A-5B, the retraction part 46 is still attached to the insertion part 50 by the two inward hooks 54—also called snap legs—at the lower end of the retraction part 46 but the inward hooks 54 are in this almost fully forwarded position in contact with two outward surfaces 64. When the inclined surface of each inward hooks 54 touches the inclined outward surface 64, the inward hooks 54 will be forced outwards as the inward hooks 54 are flexibly attached to the body of the retraction part 46 (at least the arms to which the inward hooks 54 are attached are more flexible than the protruding parts providing the outward surfaces 64) and the inward hooks 54 will be released from the downward surface 59 of the insertion part 50. Thus, the inward hooks 54 are no longer in direct contact with the downward surface 59 of the insertion part 50.

Figure 6:
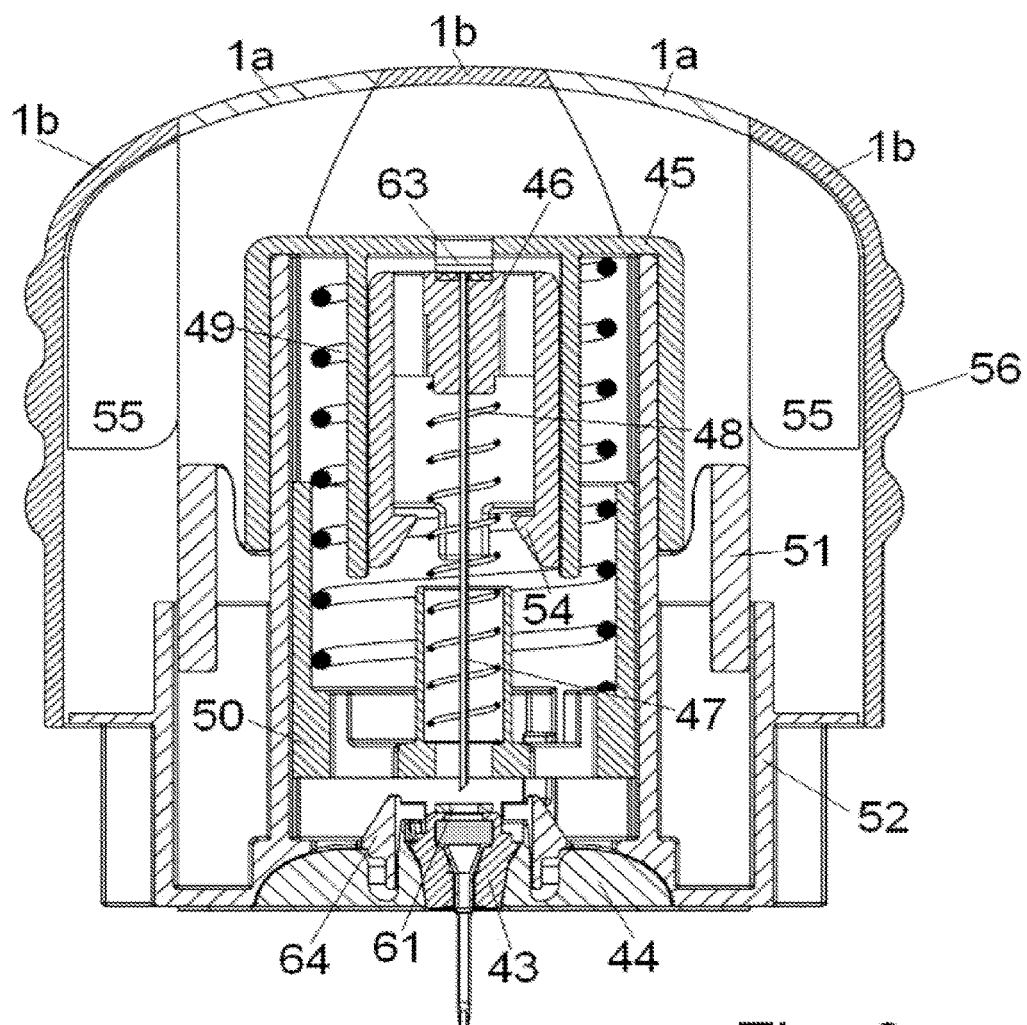
FIG. 6 shows a cut-through view along line A-A of the same embodiment as shown in FIGS. 1A-1B, 2A-2C, 3, 4, and 5A-5B in a state where a subcutaneous part has been inserted and the introducer needle has been fully retracted.

FIG. 6 shows a cut-through view along line A-A of the same embodiment as shown in FIGS. 1A-1B, 2A-2C, 3-4, and 5A-5B. The cut-through view along line A-A in FIG. 6 is from the same angle as the cut-through view in FIG. 1B and FIG. 5B, however in FIG. 6, the device is shown in a state where a subcutaneous part 43 has been inserted and the introducer needle 47 has been fully retracted. The introducer needle 47 is at this state hidden inside the housing 1 and the retraction spring 48 continues to put a slight pressure on the retraction part 46 which prevents the introducer needle 49 from falling out through the openings in the insertion part 50 and in the internal base 52.

In the state displayed in FIG. 6, the retraction part 46 is pushed to a retracted position by the retraction spring 48. Walls of the inner lid 45 extending from the upper inner surface and downwards in the insertion direction ensures that the movement of the retraction part 46 is properly guided and that the retraction part 46 moves along a straight line coinciding with the insertion direction. The insertion part 50 is in a fully forward position where the elastic unit 63 pushes against the subcutaneous part 43. The base 44 has been released from the internal base 52 and when the inserter device is removed from the site of insertion, the base 44 will remain on the patient's skin as nothing is any longer connecting the base 44 to the insertion device.

FIG. 7 shows an embodiment of an internal base 52 which can be used with the embodiments of the inserter device shown in FIGS. 1A-1B, 2A-2C, 3-4, 5A-5B, and 6. The internal base 52 is seen mainly from the lower side i.e. the side which comes into contact with the patient's skin. Normally, the base 44 is mounted in the dome-shaped receiving portion and the lower surface of the base 44 will be covered by an adhesive e.g. in the form of an adhesive surface of a mounting pad 67. The receiving portion of the internal base 52 has a central opening through which a subcutaneous part 43 can be moved to the insertion site.

It is desirable that the base 44 is somehow releasably attached to the internal base 52 of the inserter device independently of whether the base 44 is a port site or another type of medical equipment, which is to be attached to the patient's skin by the inserter device. In the embodiment of FIG. 7 this releasable attachment is provided by snap legs 65 of the internal base 52 which fit into a groove 66 in the base 44.

The outward hooks 64 of the internal base 52 is placed in openings displaced around 30° relative to the snap legs 65 but could be at any angle relative to the snap legs as long as there is enough space around each part to allow all functionalities.

FIGS. 8A-8C shows an embodiment of a base 44 in the form of a port site which can be used with the embodiment of the inserter device shown in FIGS. 1A-1B, 2A-2C, 3-4, 5A-5B, and 6. The subcutaneous part 43 is inserted in/through a central opening in the base 44. The body of the base 44, which is normally made of molded plastic, is provided with a groove 66 encircling the central opening. The groove 66 provides an edge corresponding to snap legs 65 of the internal base 52 of the inserter device; such an arrangement can assure that the medical device is released from the internal base 52 at a desired point of insertion.

Figure 9:
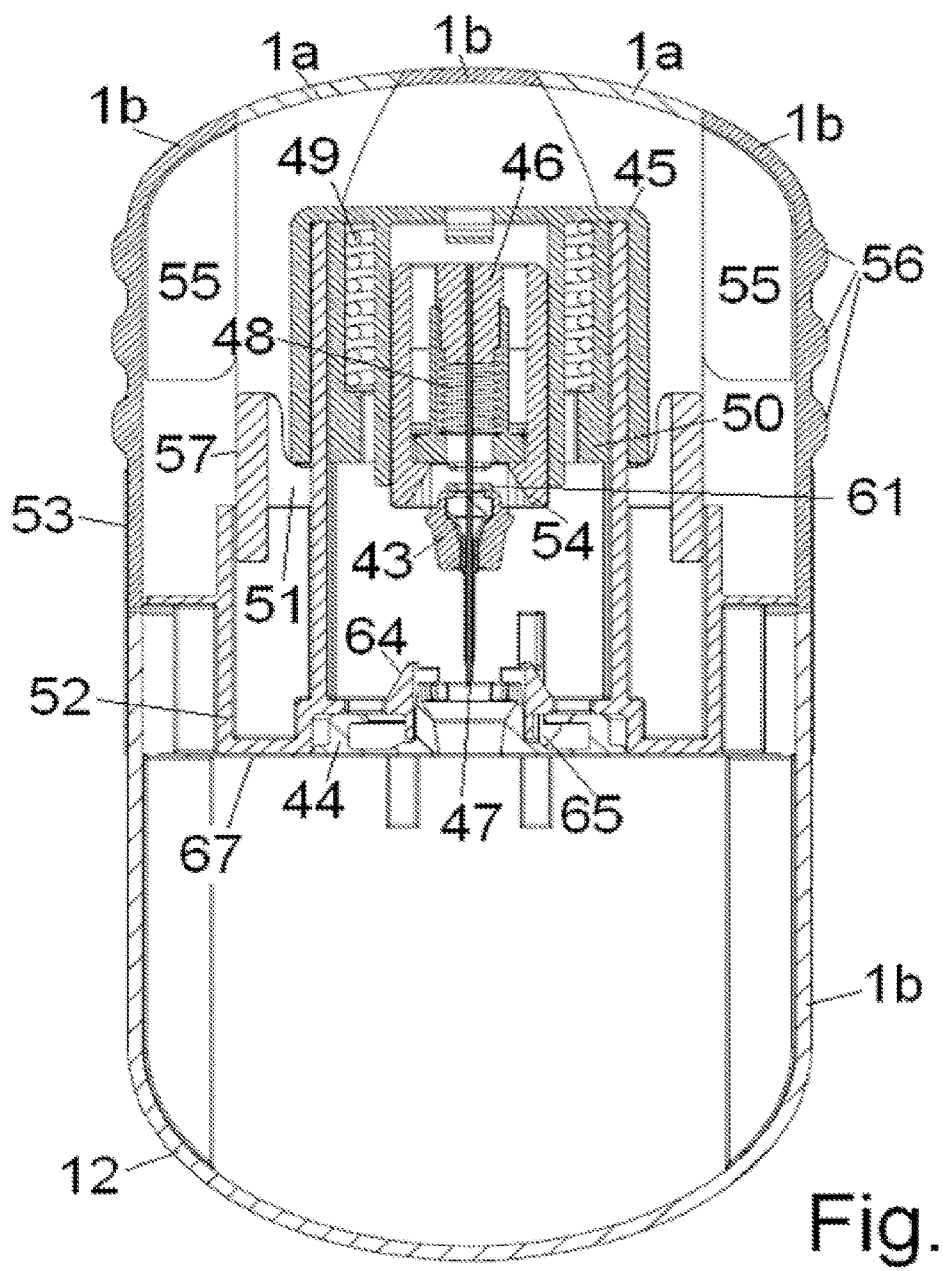
FIG. 9 shows another embodiment of an inserter device which inserter device functions in the same way as the embodiment shown in FIGS. 1A-1B, 2A-2C, 3, 4, 5A-5B, and 6 but it is directed to the insertion of another kind of medical device.

FIG. 9 illustrates second embodiment of a medical device being an inserter device. This inserter device functions in the same way as the embodiment shown in FIGS. 1A-1B, 2A-2C, 3-4, 5A-5B, and 6 but it is directed to the insertion of another kind of medical device. That the inserter device is intended to be used with another medical device results in changes in the lid 12 and the internal base 52.

The lid 12 shown in FIG. 9 is larger than the lid 12 shown in FIGS. 1A-1B, and 2A-2C, where "larger" indicates that the lid 12 constitutes a larger internal volume. This is advantageous if—as illustrated in FIG. 9—the medical device is an infusion site. During use, an infusion site will often be connected to a medication reservoir and it is thus necessary to provide the user/patient with some extra equipment in the form a tube provided with a connector. This extra equipment can beneficially be stored in the large lid 12 under sterile conditions.

The receiving portion at the lower or open end of the internal base 52 has a different shape in the embodiment shown in FIG. 9 compared to the embodiment of FIGS. 1A-1B, 2A-2C, 3-4, 5A-5B, and 6. This is caused by the fact that it is desirable to have a receiving portion which fits closely to the upper surface of the medical device. Also the release means, which cause the medical device to be released automatically during insertion of the subcutaneous part, might need to be adapted to the individual medical device.

All other units used to construct the inserter device are exactly the same as in the embodiment illustrated in FIGS. 1A-1B, 2A-2C, 3-4, 5A-5B, and 6. The same reference numbers are used in FIG. 9 as for the similar parts in FIGS. 1A-1B, 2A-2C, 3-4, 5A-5B, and 6.

FIGS. 10A-10D shows the inserter device of FIG. 9 in a first state i.e. a before-use-state where the tamperproof band 53 has not yet been removed, in a second state where the tamperproof band 53 has been removed and the device is ready to be used, and in a third state where the lid 12 has been removed and the inserter de-vice is ready to be placed against the skin of the patient.

FIGS. 11A-11C show an embodiment of an infusion site, which can be positioned with the inserter of FIG. 9. The base 44 comprises a single body which is normally moulded of a plastic material. During use this single body will be mounted on a mounting pad 67 which ensures that the base 44 stays positioned on the patient's skin. The mounting pad 67 can e.g. comprise a double adhesive pad where both the upper and the lower surface of the pad are adhesive. The upper surface of the mounting pad 67 is the surface facing the base 44 and the lower surface of the mounting pad 67 is the surface facing the patient's skin. Alternatively, the mounting pad 67 can comprise a pad having a non-adhesive upper surface and an adhesive lower surface. Whether the mounting pad 67 (also called mounting surface) comprises a double adhesive or a single sided adhesive, the mounting pad 67 normally comprises a patch of weaved or non-weaved material and is adapted to be releasably attached to the patient's skin during use e.g. by an adhesive surface facing the skin. The body of the base 44 can e.g. be made from ABS (acrylonitrile butadiene styrene) or another relatively hard and mouldable or otherwise formable material.

Figure 12:
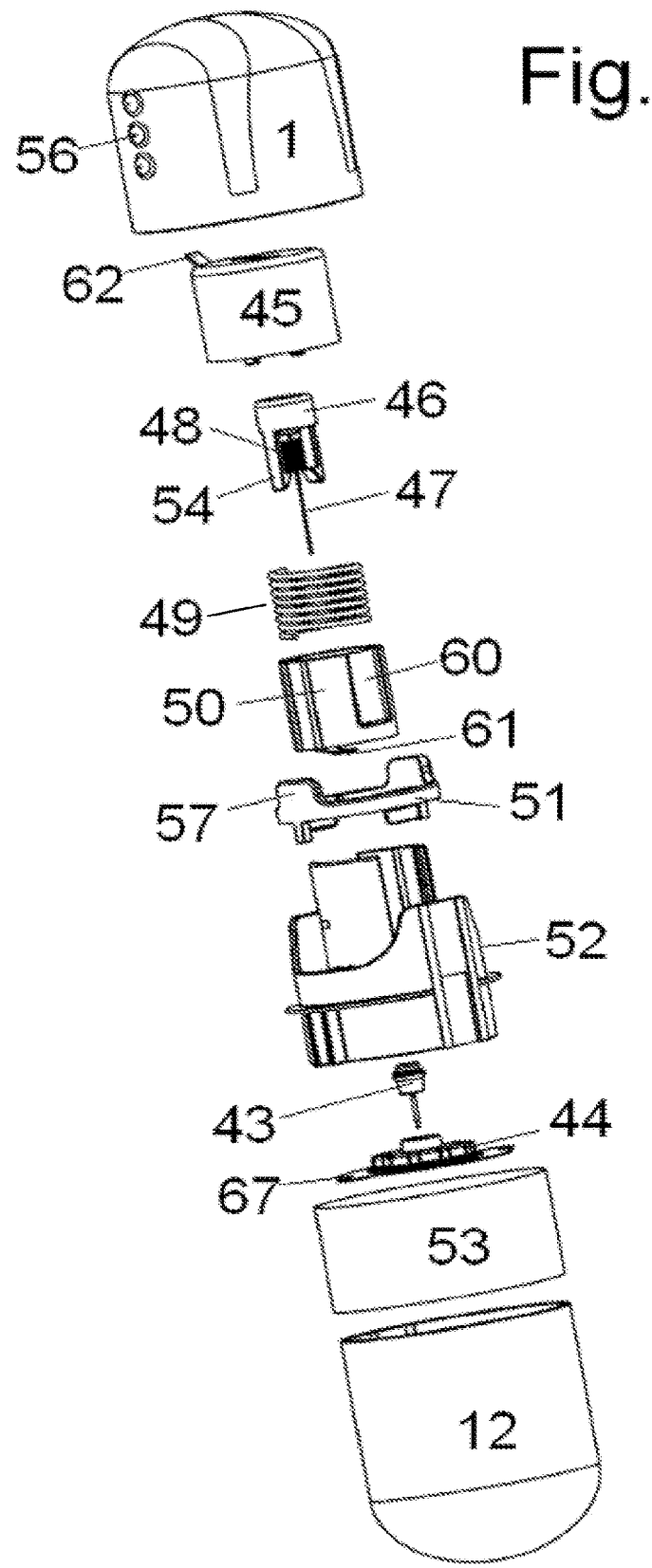
FIG. 12 shows an exploded view of all the parts of the embodiment of FIG. 9.

FIG. 12 shows an exploded view of all the parts of the embodiment of FIG. 9. The number of units is the same in the embodiment of FIGS. 1A-1B, 2A-2C, 3-4, 5A-5B, and 6 as well as the units are joined in a similar way as in the embodiment of FIGS. 1A-1B, 2A-2C, 3-4, 5A-5B, and 6, although two of the units i.e. the internal base 52 and the lid 12 are differently constructed as described previously.

Positioning procedure for the two embodiments of the medical device being an inserter device shown in FIGS. 1A-1B, 2A-2C, 3-4, 5A-5B, 6-7, 8A-8C, 9, and 10A-10D:

When using the inserter device of FIGS. 1A-1B, 2A-2C, 3-4, 5A-5B, 6-7, 8A-8C, 9, and 10A-10D and positioning a subcutaneous part, the user has to perform the following 7 steps:

1. Remove the tamperproof band 53
2. Remove the lid 12 from the housing 1 and expose the adhesive surface of the port site
3. Place the open end of the housing against the skin of the patient (the adhesive surface of the port site is adhered to the patient's skin during this step)
4. Push the housing towards the skin of the patient until it cannot be pushed further
5. Activate the actuator means by pushing at the indicated positions 56 to such a degree that the soft material in the housing is collapsing
6. Remove the inserter device from the patient's skin, e.g. re-position the lid 12 at the open end of the housing
7. Dispose of the used inserter device with or without the lid 12

FIGS. 13A-13B, 14A-14B, 15A-15B, 16A-16B, 17A-17B, 18A-18B, and 19 illustrate yet another embodiment of a medical device being an inserter device. This third embodiment is similar to the embodiment illustrated in FIGS. 8A-8C and 9, and parts similar to parts of the first and second embodiments are illustrated with the same reference numbers as used when describing these two former embodiments. The needle hub 5, the primary spring 6, and the release means 41 for the needle hub 5 are similar to the corresponding parts of the first embodiment. The embodiment of FIGS. 15A-15B, 16A-16B, 17A-17B, 18A-18B, and 19 has manual insertion and automatic retraction of the insertion needle. This embodiment comprises five separate pieces, excluding a subcutaneous part 43 and a base part 44, and all of the pieces are normally made of moulded plastic except the primary spring 6, which is e.g. made of a soft and elastic material such as a rubber band, and e.g. the insertion needle 4, which might be made of metal.

Figure 13A:
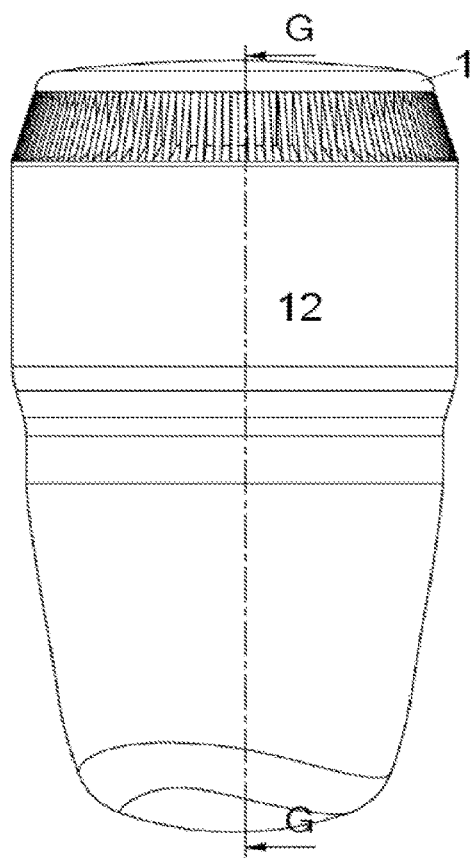
FIGS. 13A-13B shows an embodiment of the inserter device in a shelf state i.e. an unloaded and sterile state where the primary spring is constituted by a single circular elastic band.
Figure 13B:
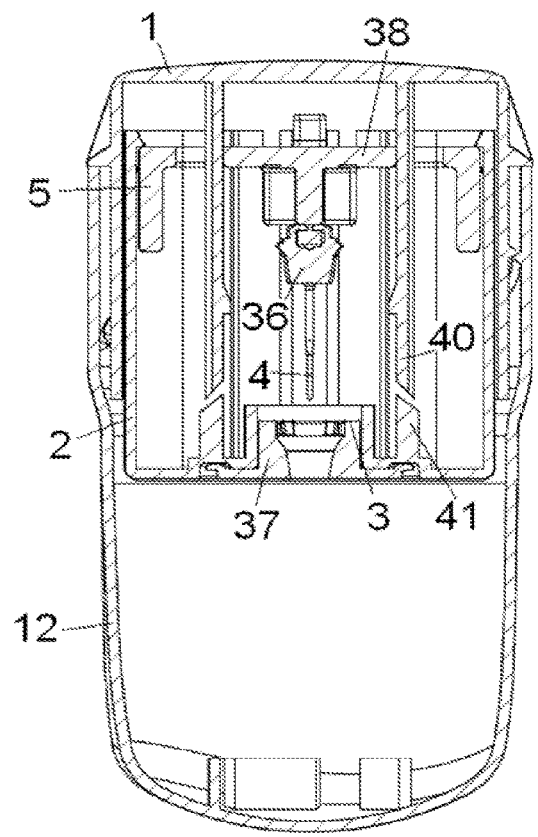
Figure 16A:
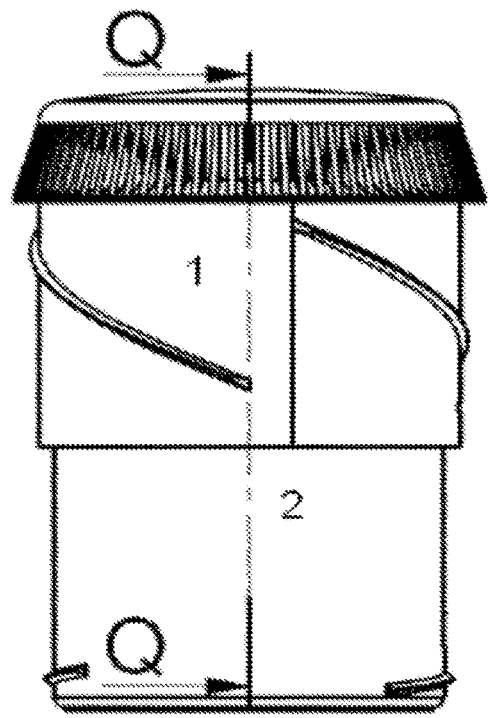
Figure 16B:
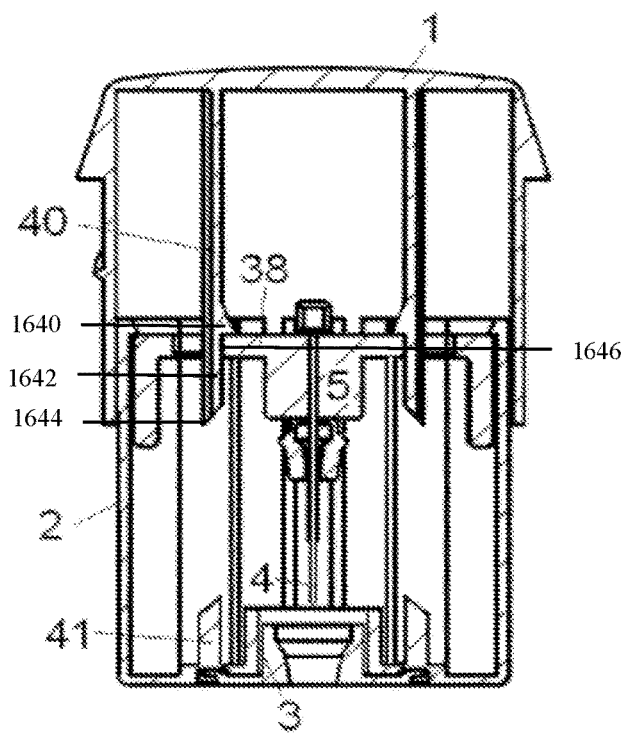

FIGS. 13A-13B shows an embodiment of the inserter device in a shelf state which is an unloaded and sterile state. The primary spring 6 (see FIG. 19) is constituted by a single circular elastic band and is attached to the top of the cover 2 corresponding to the internal base of the embodiment of FIGS. 1A-1B, 2A-2C, 3-4, 5A-5B, 6-7, 8A-8C, 9, 10A-10D, 11A-11C, and 12. The primary spring 6 supports under the needle hub 5 corresponding to the retraction part 46 of the embodiment of FIGS. 1A-1B, 2A-2C, 3-4, 5A-5B, 6-7, 8A-8C, 9, 10A-10D, 11A-11C, and 12, i.e. the primary spring 6 pulls the needle hub 5 and the top of cover 2 together. The needle hub 5 of this embodiment is constructed with a circular top plate 38 (best seen in FIG. 19) having a diameter small enough to allow the needle hub 5 to slide up and down inside the cylindrical cover 2. The circular top plate 38 has openings 39 allowing for the elastic band constituting the primary spring 6 to pass from the lower side of the needle hub 5 to the top of the cover 2 without by its presence disturbing the sliding movement of the needle hub 5 relative to the cover 2. The elastic band 6 can be attached to the top of the cover 2 by winding it around a protruding part of the edge 42; this can be done due to the flexibility of the elastic band 6. The circular top plate 38 is also provided with two openings 1646 (one of which is labeled in FIG. 16B) and a flexible loading arm 40 is provided with an inward hook 1640 and a stem 1642 interconnected with the hook 1640 that extends away from the hook 1640 to define a tip 1644 at which the arm 40 terminates. In use of the inserter device as shown in FIG. 16B, the hooks 1640 of the arms 40 directly contact an upper surface of the hub 5 and the stems 1642 of the arms 40 extend through the corresponding passages 1646 formed in the hub 5. The inserter device of FIGS. 13A-13B is provided with a lid 12, which assures sterile conditions for the internal parts of the inserter device before opening. According to the embodiment of FIGS. 13A-13B, 14A-14B, 15A-15B, 16A-16B, 17A-17B, 18A-18B, and 19, the lid 12 constitutes a volume large enough to contain a tube and appurtenant tube parts such as connector for infusion set.

FIGS. 14A-14B shows the inserter device in a side view in a pre-loading step. The inside of the inserter device, which was previously protected by the tightly combined housing 1 and lid 12, is during the pre-loading step subjected to the surrounding atmosphere. Corresponding threads on the bottom lid 12 and housing 1 lifts the housing 1 when the user twists the two parts in opposite directions. The cover 2—or internal base—is held in place by reverse direction threads between the cover 2 and the bottom lid 12. Thus, the cover 2 does not move relative to the bottom lid 12 when the housing 1 is twisted relative to the bottom lid 12. When the housing 1 is twisted e.g. around 90 degrees, the housing 1 is forced away from the cover 2 and released from the bottom lid 12. In the pre-loaded state the inserter device is ready to use.

Both FIGS. 15A-15B and FIGS. 16A-16B show cut-through views of the inserter device in the preloaded state of FIGS. 14A-14B; FIG. 15A shows a cut-through view along the line H-H of FIG. 14B and FIG. 16B shows a cut-through view along the line Q-Q in FIG. 16A. The housing 1 has been released from the lid 12 and the lid 12 has been removed. The preloading causes inward hooks of the two flexible loading arms 40 to move to the upper side of the circular top plate 38 of the needle hub 5, and due to the flexibility of the loading arms 40 the hooks are caught on top of the needle hub 5. When the device has been put into this state, the device is ready for insertion when the lid 12 has been removed from the device. Normally removal of the lid 12 will lead to that a protective layer such as a release layer is removed from the adhesive side of the medical device placed in the position 3 for the infusion site.

The housing 1 and the cover 2 have means preventing that they separate from each other. In the shown embodiment, these means has the form of a snap connection comprising an inward protruding part 68 near the lower edge of the housing 1 and an outward protruding part 69 near the top edge of the cover 2. This snap lock will prevent that the housing 1 from being disconnected from the cover 2.

FIGS. 17A-17B shows the embodiment of the inserter device in a loaded state where the primary spring is as extended as it will be during operation of the inserter device and the insertion needle 4 is fully inserted. Normally a distinct click-sound will indicate that the subcutaneous part is locked to the base and that the user can let go of the pressure keeping the needle hub 5 down. The primary spring 6 which is attached to the top of the cover 2 has been stretched to its maximum as the nee-die hub 5, which the elastic band is placed under, is at its lowest position. In this position, the release means 41 get in contact with the flexible loading arms 40 and pushes the loading arms 40 outward i.e. away from each other. This movement causes the needle hub 5 to be released from the hooks of the loading arms 40, which result in the needle hub 5 being pulled upwards to the top of the cover 2 where the opposite ends of the circular elastic band are fastened. At this position the cover 2 is locked to the housing 1.

Figure 18A:
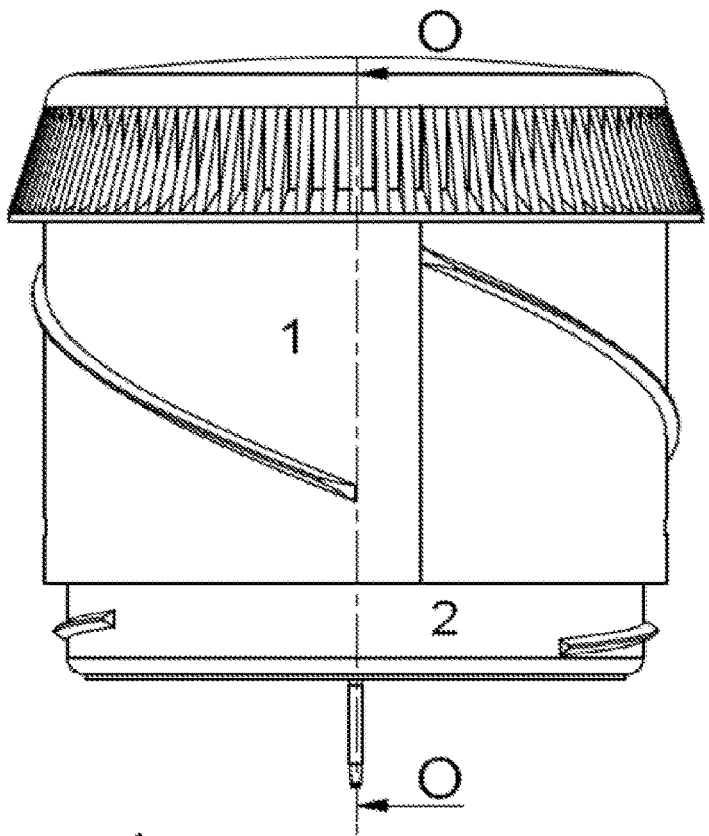
FIGS. 18A-18B shows embodiment of the inserter device in a final unloaded state.
Figure 18B:
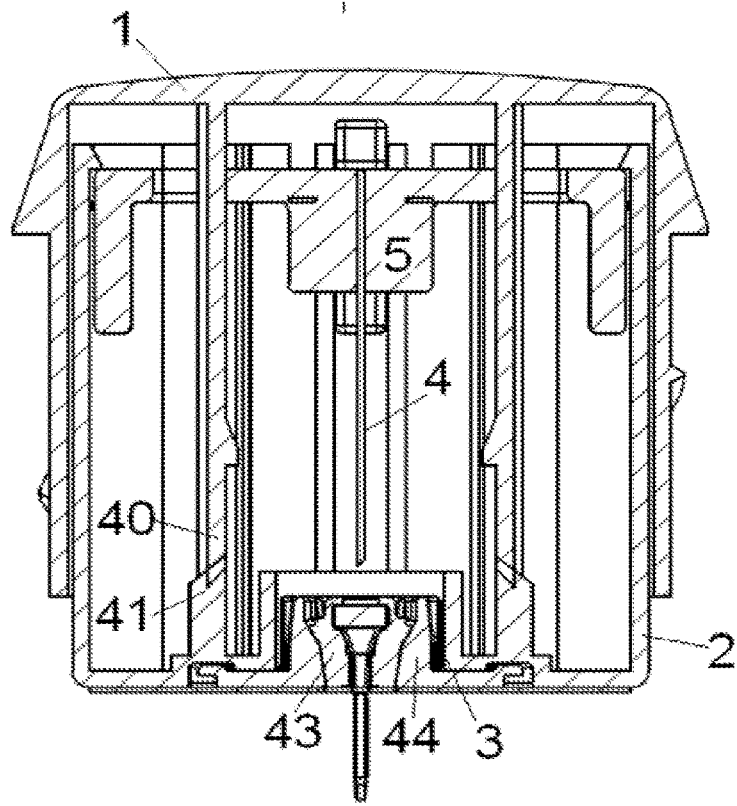

FIG. 18B shows a cut-through view along the line 0-0 in FIG. 18A where the embodiment of the inserter device is in a final unloaded state. In this state, the needle hub 5 and thereby the insertion needle 4 has been brought into a retracted position. In this retracted position, the used insertion needle 4 cannot get into contact with the surroundings because the inserter device comprises locking means locking the cover 2 is to the housing 1. According to the shown embodiment, the locking means comprises a mechanical snap lock where an inward protruding part of the cover 70 slides over a locking part 71 of the housing 1. The state is similar to the unloaded state shown in FIGS. 13A-13B except that the two part infusion device comprising the subcutaneous part 43 and the base 44 is now assembled and the subcutaneous part 43 is inserted into the base 44.

FIG. 19 shows a possible position of a primary spring 6 in the form of an elastic band such as a rubber band used with the embodiment of the inserter device. The elastic band is attached to the top of the cover 2 by wrapping parts of the elastic band around protruding parts 42 extending outward from the upper edge of the cover 2. The central plate being encompassed by the wall of the cover 2 is a circular top plate 38 of the needle hub 5 and the elastic band passes through openings 39 provided in the top of the needle hub 5 which openings are large enough to prevent the elastic band from interfering to interfere with the movement of the needle hub 5 relative to the cover 2.

FIGS. 20A-20B shows a medical device comprising a subcutaneous part 43 and an infusion site 44. The subcutaneous part 43 comprises a part, which is to be inserted subcutaneously in the patient. The subcutaneous part 43 is preloaded onto the insertion needle 4 and the infusion site 44 is attached to the cover 2 inside the position 3 for the infusion site. The inserter device might also be used for insertion of other medical devices comprising a subcutaneous part whether such a device would be in one or more pieces, and then the position 3 for the infusion site would have to be adapted to the medical device in question.

Positioning procedure for the embodiment shown in FIGS. 12,13A-13B, 14A-14B, 15A-15B, 16A-16B, 17A-17B, 18A-18B, and 19:

When using the inserter device of FIGS. 12,13A-13B, 14A-14B, 15A-15B, 16A-16B, 17A-17B, 18A-18B, and 19 and positioning a subcutaneous part, the user has to perform the following 7 steps:
1. E.g. remove tamperproof packing
2. Release the housing 1 from the lid 12 and loading the device by holding on to the lid 12 and twisting the housing 1
3. Remove the lid 12. E.g. the release paper situated on the mounting pad of the medical device is attached to the lid. When the release paper is removed together with the lid, the adhesive surface of the medical device will be exposed and ready to position on the patient
4. Position the end of the cover containing the medical device on the patient's skin
5. Press the housing 1 against the skin until a click sounds
6. Remove the inserter device from the patient's skin, e.g. re-position the lid 12 at the open end of the housing
7. Dispose of the used inserter device with or without the lid 12.

FIGS. 21A-21E, 22A-22E, 23A-23E, 24A-24B, and 25, illustrate a fourth embodiment of a medical device constituted by a site 101 and a connector part. The site 101, which is stationary during use and attached to a patients skin, comprises:
   a subcutaneous part;
   positioning means 105 configured to correspond to positioning parts 107 on the connector part to provide a user-chosen locked positioning, i.e. fixed positioning, of the connector part relative to the site 101 in a horizontal or rotational direction during use; and
   attachment means 104 configured to correspond to retaining means 114 on the connector part to provide a stationary i.e. fixed positioning of the connector part relative to the site 101 in a vertical direction during use.

The connector part, which can be attached to and detached from the site 101 after mounting the site 101 on the patients skin, comprises:

- horizontal or rotational positioning parts 107;
- vertical attachment parts 114;
- actuating means 115 which when actuated release the connector part from the site 101; and
- a cover constituting at least a part of the outer surface wherein the cover of the connector part is constructed of materials having different or varying flexibility i.e. the material(s) constituting the cover is more flexible in some areas than in other areas.

"Flexibility" defines according to the present application an ability to bend or to curve or to having a dimension of a material reduced in another way than by bending or curving e.g. by being squeezed to a higher density, and a subsequent ability to return to the original shape.

That a material is "hard" means that the material does not change its shape during normal use unless in certain flexible areas where the hard material is shaped in such a way that e.g. provided with relatively thin or narrow areas, the material will act flexible.

Figures 24A, 24B:
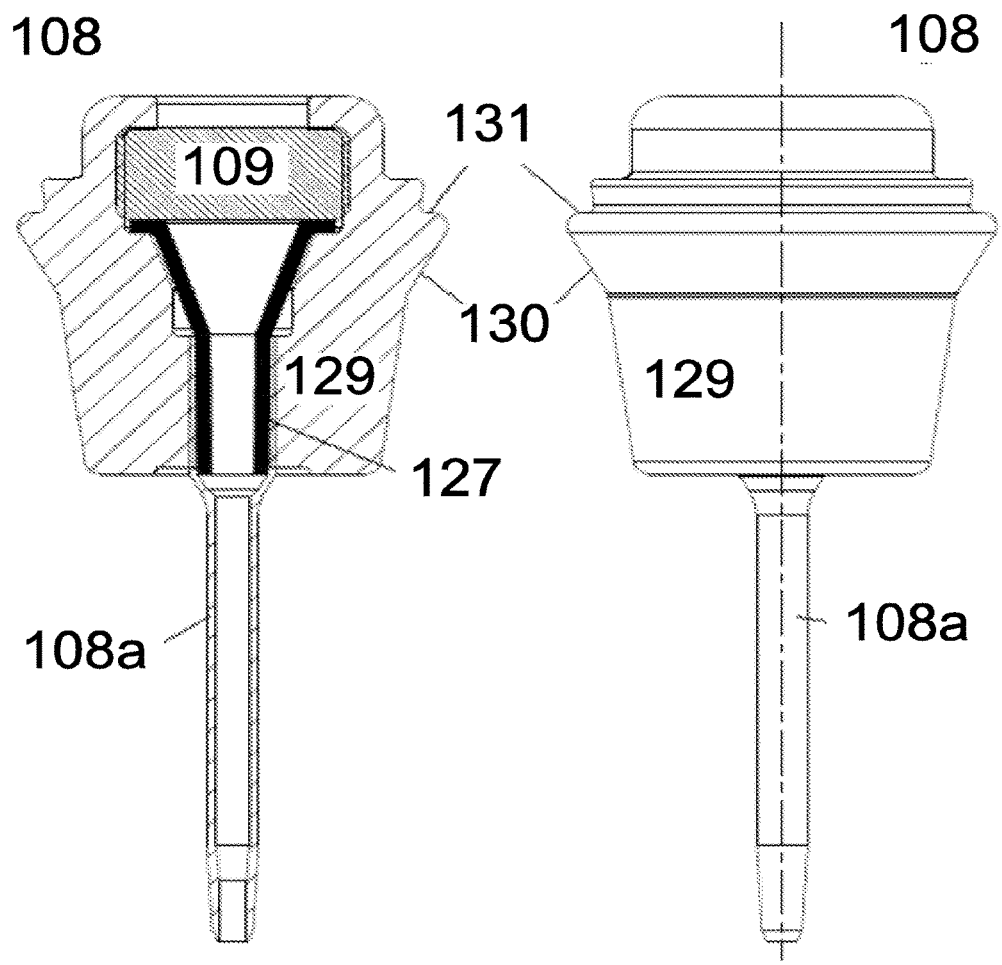
FIGS. 24A-24B respectively shows a cut-through view through the center and a side view of an embodiment of a subcutaneous part in the form of a cannula part which can be used together with any of the sites illustrated in the figures.

In more detail, the fourth embodiment of a medical device shown in FIGS. 21A-21E comprises a site 101 in the form of an infusion site which can be combined with a subcutaneous part 108 as illustrated in FIGS. 24A-24B. The site 101 as shown in FIGS. 21A-21E comprises a single part, which is normally moulded of a plastic material. During use this single part will be mounted on a mounting pad which provides for the site 101 to stay positioned on the patient's skin. The not shown mounting pad can e.g. comprise a double adhesive pad where both the upper and the lower surface of the pad are adhesive. The upper surface of the mounting pad is the surface facing the site 101 and the lower surface of the mounting pad is the sur-face facing the patient's skin. In this case the mounting pad is placed on the patients skin before or during positioning of the site 101 on the patients skin and the site 101 is attached to the upper surface of the mounting pad either before or after the mounting pad has been placed on the patients skin. Alternatively, the mounting pad can comprise a pad having a non-adhesive upper surface and an adhesive lower surface. Whether the mounting pad (also called mounting surface) comprises a double adhesive or a single sided adhesive, the mounting pad normally comprises a patch of weaved or non-weaved material and is adapted to be releasably attached to the patient's skin during use e.g. by an adhesive surface facing the skin. The site 101 can e.g. be made from ABS (acrylonitrile butadiene styrene) or another relatively hard and mouldable or otherwise formable material.

FIG. 21A shows the site 101 seen from the lower side i.e. the side which is facing the patient's skin during use. In FIG. 21A an area is marked with a grey colour. This is the part of the site which is in direct contact with (i.e. touches) the mounting pad during use. According to the embodiment shown in FIG. 21A this area comprises a central circular part 121 having a central opening 122 through which the subcutaneous part 108 can be inserted. The area also has peripheral protrusions 123—five peripheral protrusions 123 according to this embodiment—connecting the central circular part 121 to a peripheral circular part 124. From this side it is also possible to see the attachment means 104 for the connector part in the form of an inwardly i.e. towards the center protruding edge. As the central circular part 121 is connected to the peripheral circular part 124 through two or more peripheral protrusions 123, the construction is very flexible and it is less likely that a force applied to the connector part, which during use is fastened to the peripheral circular part 124, is passed to the central circular part 121 holding the subcutaneous part 108.

FIG. 21B shows the site 101 seen from the upper side i.e. the side of the device facing in a direction opposite the patient's skin. From this side it is possible to see the circular or ring-shaped part 110, which is attached to or placed on top of the peripheral circular part 124, and the central part 111, which is attached to or placed on top of the central circular part 121 and which further is adapted to hold the subcutaneous part 108 during use.

The site 101 comprises positioning means 105 corresponding to positioning means 107 on a connector part. According to the fourth embodiment of the medical device shown in FIGS. 21A-21E, the positioning means 105 are part of the circular part 110 and are placed along or are a part of the periphery of the circular part 110. The shown embodiment comprises ten positioning means 105 having the form of recesses in the outer surface of the circular part 110. The positioning means 105 are referred to as recesses compared to the outer circumference of the peripheral circular part 124. Generally, the positioning means 105 comprises two or more recesses that can be combined with protruding parts 107 of a corresponding connector part. Further, the positioning means 105 are provided in a hard part of the infusion site 101, where the hard parts of the site are e.g. the circular part 110 or e.g. the central part 111.

The central part 111 comprises an opening 112 or cavity, adapted to accommodate at least a portion of a subcutaneous part 108, essentially the portion of the subcutaneous part 108 which is not inserted or to be inserted in the patient's skin. According to this embodiment, the opening 112 comprises attachment means 125 for the subcutaneous part 108 adapted to provide a non-releasable connection between the site 101 and the subcutaneous part 108 during use. The subcutaneous part 108 comprises corresponding means for attachment to the opening 112. According to this fourth embodiment, the attachment means 125 have the form of four parts protruding from each their position of the inner upright wall of the central part 111. The attachment means 125 are compliant, which means that the attachment means 125 are either made of an elastic material or at least part (or all) of the attachments means 125 can be moved outwards due to a flexibility of the construction of the attachment means 125. Here "elastic" means that the dimensions of the material can be reduced when a pressure is applied to the material and afterwards the material return to the original size and position for all practical means. In both cases the diameter of the internal opening in the central part 111 can be varied as a result of pressure applied in a radial outward direction toward the inner surface of the upright central part 111.

The circular part 110 with the positioning means 105 is shaped like a symmetric toothed wheel having ten teeth with rounded off recesses provided in between the teeth. Each recess has identical dimensions, and a given area comprising both an opening and a surrounding part of a protruding area fits closely to a corresponding area on the proximal side of the connector part. The corresponding means 107 for positioning of the connector part are adapted to fit into one or more of the openings of the positioning means 105, whereby ten distinct and different relative positions of the connector part in correspondence to the site 101 are possible. The toothed wheel will normally have 3-20 openings, thereby providing 3-20 different positions of the connector part relative to the site 101. The openings of the toothed wheel might have a less rounded shape comprising straighter edges, such as triangular or rectangular openings. Accordingly, the means for positioning 107 will have a corresponding shape, such as a triangular or rectangular shape, respectively.

FIG. 21C shows the site from a cut-through view along the line A-A of FIG. 21A. FIG. 21D shows a side view of the device. FIG. 21E shows an upper view of the site i.e. the side turned away from the patient's skin during use.

Figure 22A:
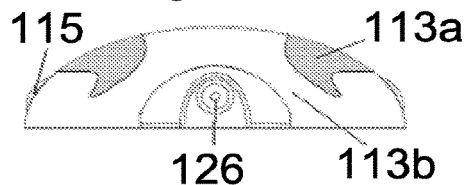
FIGS. 22A-22E show an embodiment of a connector part that can be used together with the sites of FIGS. 21A-21E.
Figure 22D:
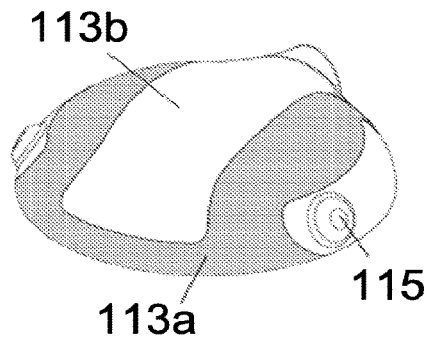
Figure 22B:
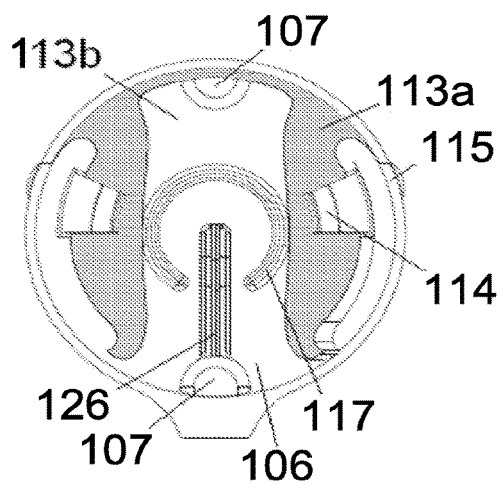
Figure 22E:
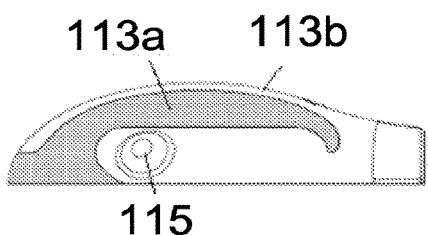
Figure 22C:
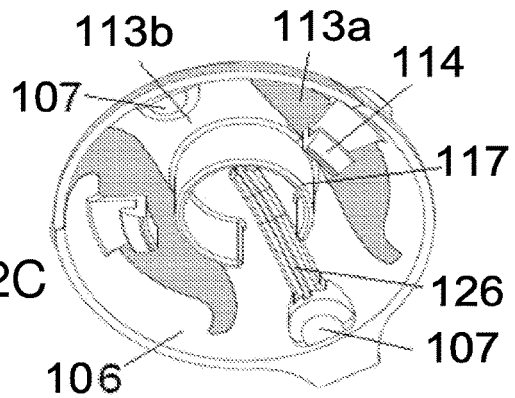

FIGS. 22A-22E show an embodiment of a connector part that can be used together with the infusion site 44 of FIG. 11A and FIGS. 21A-21E. The embodiment of FIGS. 11A-11C corresponds to the embodiment of an infusion site shown in FIG. 1 in European patent application no. 0964041 and the description of this embodiment is hereby incorporated by reference. More specifically, FIG. 22A shows the connector part seen from the tube side, i.e. the side to which a tube element will be connected to the device during use. FIG. 22B shows the connector part from the lower side i.e. the side which is covered by the mounting pad during use. From this position it can be seen how the arms 115 can be elastically hinged to the central part of the attachment means 106. FIG. 22C also shows the connector part from the lower side but in an inclined angle which makes it possible to see how the retaining means 114 are provided with an upward facing surface. FIG. 22D shows the connector part seen from above from the side opposite the tube connection. From this angle it is possible to see that only one continuous area of soft flexible/elastic material 113a is provided with this embodiment. FIG. 22E shows the connector part seen from the side where the connector needle 126 opens out is to the right.

The connector part shown in FIGS. 22A-22E comprises an outer shell having an inner cavity and is adapted to encompass the site 101 of FIGS. 21A-21E. The outer shell of the embodiment of FIGS. 22A-22E is not exclusively made of a hard material. The outer shell of the embodiment shown in FIGS. 22A-22E provides a rounded and continuous surface and is a composite of one or more parts of hard material combined with one or more areas of a soft and/or elastic material. The areas of soft material are referred to as 113a and the areas of hard material are referred to as 113b in FIGS. 22A-22E.

According to an embodiment, the connector part can be moulded in ABS (acrylonitrile butadiene styrene) and TPE (thermoplastic elastomer) where the ABS part provides as a hard shell or skeleton including snap legs 114, 115 and knobs i.e. positioning means 107 that can secure the connector in one of the ten possible positions. According to this embodiment, the TPE i.e. the soft material is just covering the gab that makes it possible to flex i.e. push the arms 115 together. This leaves the highest point in the connector free of TPE which can be advantages as the ABS parts has a lower coefficient of friction which means that e.g. clothes does not as easily cling to the set.

The attachment means 106 of the embodiment of FIGS. 22A-22E do not need to be elastic, as the elasticity needed to bring the arms 115 back to the point of departure can be provided by a soft and elastic material positioned in between the areas of the arms 115 and the central part of hard material, i.e. the central part to which the connector needle 126 is fastened. Normally the soft material 113a is simply flexible and not elastic, i.e. it does not have the ability to provide the force to push the arms 115 back to the original position. The force for returning the arms 115 to the original position is then provided by the elasticity of the attachments means 106 comprising both the arms 115 and the central part providing fastening positions for the connector needle 126 and for each of the arms 115. The arms 115 are provided with retaining means 114 in the form of outward hooks 114 having upward surfaces which upward surfaces during interlocking with the site 101 rest against the downward surface of the attachment means 104 of the site 101. The interlocking of the connector part and the site 101 is released when the arms 115 are simultaneously are pushed toward the center i.e. inwards.

When activating the attachment means 106, the connector part can be attached to or detached from the site 101. Activating the attachment means 106 also makes it possible to place the interacting means for positioning 107 of the connector part relative to the positioning means 105 of the site 101 in a distinct user-defined position. According to the shown embodiment the user can choose any desired position out of the ten possible.

The means for attachment 106 of the connector part comprise actuating means in the form of arms 115, retaining elements in the form of outward hooks 114, and an elastic element 116, wherein the elasticity is the result of the chosen material and the constructions, especially the diameter of the material in the area where the arms 115 are joined to the central part 117. The actuating means 115 comprises two arms positioned diametrically opposite each other and each arm is provided with an outward hook constituting a retaining element 114. Each hook has a portion which upon release is caught under the protruding upper edge of the circular part 110 and prevents the connector part from moving away in a vertical direction. The two arms 115 of the actuating means form part of the outer shell of the connector part and will normally be provided with a section having an increased diameter or cross-section or an otherwise marked area which will make it possible for the user to feel exactly where to push in order to release/attach the connector part from the site 101. The elastic element 116 connects the two arms by one end of each arm. When the two arms 115 forming the actuating means are pressed towards each other, the elastic element will provide a spring action trying to return the arms 115 to their original relaxed position i.e. the starting point. The three elements: actuating means 115, retaining elements 114 and elastic element 116 can be moulded as a single element.

FIGS. 23A-23E show a fifth embodiment of a connector part that can be used together with the sites 101 of FIGS. 21A-21E. Functionally the connector part of FIGS. 23A-23E is very similar to the connector part illustrated in FIGS. 22A-22E, and functionally identical parts of FIGS. 23A-23E are provided with the same reference numbers as the parts of FIGS. 22A-22E.

More specifically, FIG. 23A shows the fifth embodiment of the connector part from the lower side i.e. the side which is covered by the mounting pad during use. The flexible outer shell 113a is provided with a grey colour in order to make it easier to differentiate between the outer shell 113a and the inner attachment means 106 which are kept in white colour. On the outer shell 113a, the touch point on the free end of each arm 115 is marked by three protruding points on opposite sides of the outer shell, thereby indicating to the user where to provide a pressure in order to attach or release the connector part from the site 101. FIG. 23B shows the connector part seen from the tube side, i.e. the side to which the tube element 118 is normally connected to the device during use. FIG. 23C shows the connector part seen from the side where the connector needle 126 opens out is to the left. FIG. 23D shows the connector part seen from above from the side opposite the tube connection. From this angle it is possible to see that the whole outer surface is covered with a continuous layer of material only interrupted by the protruding parts indication where the user has to put pressure on in order to release the connector part from the site. FIG. 23E shows the connector part from the lower side but in an inclined angle which makes it possible to the how the retaining means 114 are provided with an upward facing surface.

The connector part shown in FIGS. 23A-23E comprises a smooth outer shell 113a made of a flexible material and having an inner cavity adapted to encompass the site 101 of FIGS. 21A-21E. Further, the outer shell 113a of flexible material can encompass attachment means 106 comprising arms 115 provided with retaining means 114 of same type as shown and described in connection with FIGS. 22A-22E, a central piece which supports the connector needle 126, and an elastic element 116. If the attachment means 106 consist of a single piece of moulded plastic material, the elastic element 116 can be provided by a reduced material thickness at the position where each arm 115 is connected to the central piece of the attachment means 106. The elastic element can e.g. be made of ABS.

The fully covering outer shell of flexible material 113a provides a smooth surface without protruding parts that can get caught e.g. in passing clothes and the smooth surface therefore reduce the risk of having the site 101 and the attached subcutaneous part pulled out before it is desired. The soft material completely covering the surface might be made of TPE (thermoplastic elastomer). When the soft material covers the complete surface, the soft material has a larger area where it can displace i.e. fold when the connector is flexed i.e. the arms 115 are pushed together. This embodiment also results in a very simple and smooth look which leaves many possibilities for eye-catching design.

FIGS. 24A-24B shows respectively a cut-through view through the center and a side view of an embodiment of cannula part 108 which can be used together with any of the infusion sites 44, 101 illustrated in the figures. The cannula part 108 comprises a body part 129 having a through going opening allowing passage of fluid. In order to prevent access of micro organisms from the surroundings after mounting of the cannula part 108, the through going opening at the inlet end is closed with a septum 109, which allows access of 1) needles such as insertion needles providing subcutaneous positioning of the device, 2) injection needles delivering a single portion of fluid, or 3) a connector needle 129 as illustrated in the embodiments of the connector part. The septum 109 will normally be a self closing septum, i.e. when a needle has been inserted through the septum 109 and afterwards removed, the septum 109 will close and prevent access of micro organisms.

A catheter or cannula 108a extends from the outlet end of the body part 129, where the catheter might be either soft/flexible, which means that is has to be inserted with an insertion needle, or it might be a hard and self-penetrating catheter. The catheter 108a normally extends 8-10 mm from the lower surface of the body part 129 and reaches the bloodstream of the patient. The catheter 108a is attached inside the through going opening of the body part 129, and according to the shown embodiment, the catheter 108a is attached to the body part 129 by having a bushing 127 pushed into the upper open end thereby squeezing the walls of the upper end of the catheter 108a against the inner walls of the through going opening.

The bushing 127 is constituted by a tubular piece which is open for fluid in both ends, i.e. a fluid path is formed through the bushing 127. According to the shown embodiment, the bushing 127 comprises a tube part formed as a truncated cone having a decreasing diameter extended into or in contact with a cylindrical tube part. According to one embodiment, the bushing 127 is normally formed of a material e.g. steel which cannot be penetrated by an insertion needle. This feature makes it possible to operate the site 101 as a port i.e. to insert and inject fluid, e.g. by a syringe through the septum 109, without having to worry about the walls of the body part 129 or the catheter 108a being penetrated and thereby destroyed by the needle.

The outer surface of the body part 129 is normally round having varying diameter from the inlet end, i.e. where the septum 109 covers the opening, to the outlet end wherefrom the catheter 108a extends. The varying diameter provides horizontal 131 and inclined surfaces 130, where at least one of the horizontal sur-faces 131 can provide a contact surface for attachment means 125 of the site 101. "Horizontal" in this connection means that the surface is parallel to the skin surface of the patient at or around the position where the subcutaneous part is inserted. The inclined surfaces 130 support the positioning procedure when a subcutaneous part 108, 108a is injected into the correct position. Alternatively, inclined surfaces, such as the lowest part of the body 129 of the subcutaneous part 108 corresponding to inclined surfaces of the lowest part of the opening 112 in the site, can also be used to provide fastening to the site 101, as the inclined surfaces of the subcutaneous part 108, 108a can be constructed to fit closely into the opening of the site 101 in such a way that friction between the two parts locks the subcutaneous part in the site 101. Yet an alternative way of attaching the subcutaneous part 108, 108a to the site 101 is to place adhesive on one or more corresponding surfaces respectively on the subcutaneous part 108, 108a or on the site 101.

FIG. 25A shows a side view of a connector needle 26 which can be used together with the embodiment of the connector part 2 shown in FIGS. 22A-22E and 23A-23E, and FIG. 25B shows a cut-through view of a site 1 on which a connector part 2 as shown in FIGS. 22A-22E is mounted.

The embodiment of the connector needle 126 shown in FIG. 25A is made of a hard material such as steel or another material with similar mechanical properties and should be able to penetrate the septum 109 of the cannula part 108 and extend into the open space formed in the through going opening of the body part 129 of the cannula part 108. According to the shown embodiment this open part is formed in the upper truncated cone shape of the bushing 127. The connector needle 126 can be formed of a single steel needle bended in the areas 126f, 126d, and 126b as illustrated in the figure combined with the straight pieces 126g which comprises the inlet end, 126e, 126c and 126a, where 126a comprise the outlet end. The inlet end of the connector needle 126 (open end of piece 126g) might be pointed or blunt depending on how the connecting tube is constructed and the outlet end (the open end of the piece 126a) could also be either pointed or blunt depending on what it takes to penetrate the septum 109.

FIG. 25B shows a cut-through view of a site of the type shown in FIGS. 21A-21E combined with a connector part of the type shown in FIGS. 22A-22E. A tube has not been joined to the inlet end 126g of the connector needle 126 although this will normally be the case during use. The body part 129 of the cannula part 108 is locked in the shown position due to the protruding attachments means 125 which lower surface, i.e. the contact surface 128, rests against the upward facing locking surface 131 of the body part 129. A locking surface 131 formed by a horizontal contact surface extends as an unbroken circle around the periphery of the body part 129 and therefore a part of the locking surface 131 will always be positioned in front of or opposite each of the attachment means 125.

LIST OF REFERENCES 1 housing
1a sections of a soft material such as TPE
1b sections of a hard material such as ABS
2 cover
3 position for infusion site
4 insertion needle
5 needle hub
6 primary spring
12 lid
36 subcutaneous part of the third embodiment
37 base part/infusion site of the third embodiment
38 circular top plate of the third embodiment
39 opening in the circular top plate of the third embodiment 40 flexible loading arm of the third embodiment
41 release means of the third embodiment
42 protruding part of the edge
43 subcutaneous part
44 base part/infusion site
45 inner lid
46 retraction part
47 introducer needle
48 retraction spring
49 insertion spring
50 insertion part
51 release part
52 internal base
53 tamperproof band
54 inward hook of retraction part
55 protruding part on the inner surface of the housing
56 position indicators for activation
57 push position on release part
58 protruding part of the release part
59 downward facing contact surface of the insertion part 60 groove in the outer surface of the insertion part
61 means for releasing the subcutaneous part
62 plastic spring
63 elastic unit
64 outward surface of internal base
65 snap leg of internal surface
66 groove in base
67 mounting pad
68 inward protruding part of the housing
69 outward protruding part of the cover 70 inward protruding part of the cover
71 locking part of the housing
101 site of a medical device
connector part
103 mounting pad
104 attachment means on the site
105 positioning means on the site
106 attachment means of the connector part
107 positioning parts on the connector part
108 subcutaneous part
108a catheter or cannula
109 septum
110 circular or ring-shaped part on the site
111 central part on the site
112 opening on the site
113a areas of soft material such as TPE
113b areas of hard material such as ABS
114 retaining means on the connector part
115 actuating means on the connector part
116 elastic element on the connector part 117 central part on the connector part
118 tube element
121 central circular part on the site
122 central opening on the site
123 peripheral protrusion on the site
124 peripheral circular part on the site 125 attachment means on the site
126 connector needle
126a straight piece, outlet end
126b bended area
126c straight piece
126d bended area
126e straight piece
126f bended area
126g straight piece, inlet end
127 bushing
128 contact surface of the attachment means on the site
129 body part of the subcutaneous part
130 horizontal surface of the body part
131 inclined surfaces/locking surface of the body part

The invention claimed is:

1. A medical device comprising:
an outer part including a housing that provides a rounded and continuous surface, wherein the outer part provides a functional cover and comprises an inner surface and an outer surface, wherein a plurality of flexible arms are pivotally attached to or integrally formed with the inner surface, and wherein each arm of the plurality of flexible arms includes a hook and a stem interconnected with the hook that extends away from the hook to define a tip at which the arm terminates;
a spring; and
an inner part protected by the functional cover during use, wherein the outer part and the plurality of flexible arms are rotatable relative to the inner part to preload the medical device prior to use thereof, wherein the outer part comprises an activation point on a first section of the outer surface of the outer part to which pressure may be applied to cause the plurality of flexible arms to directly contact a hub subsequent to rotation of the outer part and the plurality of flexible arms relative to the inner part in such a way that pressure on the activation point initiates a function of the hub; wherein the hub is slidably attached to the inner part and the hub has at least one retracted position and at least one forward position relative to the inner part; wherein the hub is contactable by the spring in such a way that the spring is in an unloaded position when the hub is in the at least one retracted position and in a loaded position when the hub is in the at least one forward position; wherein in use of the medical device, direct contact between the plurality of flexible arms and the hub drives translation of the hub toward a user in a direction of insertion; and wherein in use of the medical device, the hooks of the plurality of flexible arms directly contact an upper surface of the hub and the stems of the plurality of flexible arms extend through corresponding passages formed in the hub to drive translation of the hub toward the user in the direction of insertion.

2. The medical device according to claim 1, wherein the outer part comprises ABS (acrylonitrile butadiene styrene).

3. The medical device according to claim 1, wherein the spring can be displaced from the loaded position to the unloaded position by exerting pressure on the activation point.

4. The medical device according to claim 1, wherein the inner part comprises a subcutaneously positionable cannula and/or sensor during use.

5. The medical device according to claim 4, wherein the outer part fully covers a site when mounted on the site.

6. A medical device comprising:
a housing including an exterior surface and an interior surface arranged opposite the exterior surface, wherein a plurality of flexible arms are integrally formed with the interior surface, and wherein each arm of the plurality of flexible arms includes a hook and a stem interconnected with the hook that extends away from the hook to define a tip at which the arm terminates;
a cover at least partially received in an interior space defined by the housing; and
a needle hub slidably coupled to the cover for movement relative thereto,
wherein the housing and the plurality of flexible arms are rotatable relative to the cover to preload the medical device prior to use thereof, wherein during use of the medical device, the plurality of flexible arms directly contact the needle hub subsequent to rotation of the housing and the plurality of flexible arms relative to the cover to cause movement of the needle hub relative to the cover, wherein the housing and the plurality of flexible arms are rotatable approximately 90 degrees relative to the cover to preload the medical device prior to use thereof, wherein in use of the medical device, direct contact between the plurality of flexible arms and the needle hub drives translation of the needle hub toward a user in a direction of insertion, and wherein in use of the medical device, the hooks of the plurality of flexible arms directly contact an upper surface of the needle hub and the stems of the plurality of flexible arms extend through corresponding passages formed in the needle hub to drive translation of the needle hub toward the user in the direction of insertion.

7. The medical device of claim 6, wherein the needle hub includes a circular plate that defines an uppermost end of the needle hub and is formed to include at least one opening, and wherein a portion of a spring of the medical device is received in the at least one opening.

8. The medical device of claim 7, wherein the cover includes at least one protrusion located adjacent the at least one opening formed in the circular plate, and wherein the spring is wound around the at least one protrusion to couple the spring to the cover.

9. The medical device of claim 8, wherein the needle hub includes at least one pedestal extending outwardly away from the circular plate, and wherein the spring is wound around the at least one pedestal to couple the spring to the needle hub.

10. The medical device of claim 6, further comprising a retraction spring, wherein the needle hub is movable relative to the cover between at least one retracted position and at least one forward position, and wherein the needle hub is contactable by the retraction spring such that the retraction spring is in an unloaded position when the needle hub is in the at least one retracted position and in a loaded position when the needle hub is in the at least one forward position.

11. The medical device of claim 6, wherein the housing is formed to include a housing projection extending inwardly toward the interior space adjacent a lowermost end of the housing, wherein the cover is formed to include a cover projection extending outwardly away from the interior space adjacent an uppermost end of the cover, and wherein the housing projection and the cover projection are configured for interaction to provide a snap lock connection that resists separation of the cover from the housing in use of the medical device.

12. A medical device comprising:
a housing including an outer surface and an inner surface arranged opposite the outer surface, wherein a plurality of flexible arms are integrally formed with the inner surface, wherein each arm of the plurality of flexible arms includes a hook and a stem interconnected with the hook that extends away from the hook to define a tip at which the arm terminates, and wherein the housing provides a rounded and continuous surface;
a cover at least partially received in an interior space defined by the housing;
a needle hub slidably coupled to the cover for movement relative thereto that includes a circular plate defining an uppermost end of the needle hub; and
a spring coupled to the cover and the circular plate of the needle hub,
wherein the housing and the plurality of flexible arms are rotatable relative to the cover to preload the medical device prior to use thereof, wherein during use of the medical device, the plurality of flexible arms directly contact the circular plate of the needle hub subsequent to rotation of the housing and the plurality of flexible arms relative to the cover to cause movement of the needle hub relative to the cover, wherein the housing and the plurality of flexible arms are rotatable approximately 90 degrees relative to the cover to preload the medical device prior to use thereof, wherein in use of the medical device, direct contact between the plurality of flexible arms and the circular plate of the needle hub drives translation of the needle hub toward a user in a direction of insertion, and wherein in use of the medical device, the hooks of the plurality of flexible arms directly contact an upper surface of the circular plate and the stems of the plurality of flexible arms extend through corresponding passages formed in the circular plate to drive translation of the needle hub toward the user in the direction of insertion.

13. The medical device of claim 12, wherein the circular plate is formed to include at least one opening and a portion of the spring is received in the at least one opening.

14. The medical device of claim 13, wherein the cover includes at least one protrusion located adjacent the at least one opening formed in the circular plate, and wherein the spring is wound around the at least one protrusion to couple the spring to the cover.

15. The medical device of claim 14, wherein the needle hub includes at least one pedestal extending outwardly away from the circular plate, and wherein the spring is wound around the at least one pedestal to couple the spring to the needle hub.

16. The medical device of claim 15, wherein the at least one pedestal of the needle hub is arranged between two protrusions of the cover, and wherein the spring is wound around the at least one pedestal and the two protrusions to couple the spring to the cover and the circular plate of the needle hub.

17. The medical device of claim 12, wherein the housing is formed to include a housing projection extending inwardly toward the interior space adjacent a lowermost end of the housing, wherein the cover is formed to include a cover projection extending outwardly away from the interior space adjacent an uppermost end of the cover, and wherein the housing projection and the cover projection are configured for interaction to provide a snap lock connection that resists separation of the cover from the housing in use of the medical device.

\* \* \* \* \*